(12) United States Patent
Fujimoto et al.

(10) Patent No.: US 12,004,888 B2
(45) Date of Patent: Jun. 11, 2024

(54) INFORMATION PROCESSING DEVICE, INFORMATION PROCESSING METHOD, AND INFORMATION PROCESSING PROGRAM

(71) Applicant: FUJIFILM CORPORATION, Tokyo (JP)

(72) Inventors: Yoshie Fujimoto, Kanagawa (JP); Shinichiro Konno, Kanagawa (JP); Shunsuke Kodaira, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 277 days.

(21) Appl. No.: 17/485,530

(22) Filed: Sep. 27, 2021

(65) Prior Publication Data
US 2022/0096025 A1 Mar. 31, 2022

(30) Foreign Application Priority Data

Sep. 30, 2020 (JP) .................................. 2020-166465

(51) Int. Cl.
*A61B 6/04* (2006.01)
*A61B 6/08* (2006.01)
(Continued)

(52) U.S. Cl.
CPC .............. *A61B 6/08* (2013.01); *A61B 6/0414* (2013.01); *A61B 6/461* (2013.01); *A61B 6/502* (2013.01);
(Continued)

(58) Field of Classification Search
None
See application file for complete search history.

(56) References Cited

U.S. PATENT DOCUMENTS 7,878,710 B2 * 2/2011 Kashiwagi ............. A61B 6/502
378/206
7,974,378 B2 * 7/2011 Fischer .................... A61B 6/08
378/205
(Continued)

FOREIGN PATENT DOCUMENTS

JP 2007-236805 A 9/2007
JP 2008-086389 A 4/2008
(Continued)

OTHER PUBLICATIONS

English language translation of the following: Office action dated Apr. 18, 2023 from the JPO in a Japanese patent application No. 2020-166465 corresponding to the instant patent application. This office action translation is submitted now in order to supplement the understanding of the cited references which are being disclosed in the instant Information Disclosure Statement.

*Primary Examiner* — Thomas R Artman
(74) *Attorney, Agent, or Firm* — SOLARIS Intellectual Property Group, PLLC

(57) ABSTRACT

An information processing device including at least one processor, wherein the processor is configured to: acquire distance information indicating a projection distance, which is a distance from an image projection unit that projects a projection image onto a projection surface of a compression member to the projection surface, in a mammography apparatus that irradiates a breast compressed by the compression member with radiation to capture a radiographic image; and control the image projection unit such that the projection image having a size corresponding to the projection distance indicated by the distance information is projected onto the projection surface in a case in which the image projection unit projects the projection image at a magnification corresponding to the projection distance.

12 Claims, 22 Drawing Sheets

(51) Int. Cl.
*A61B 6/46* (2024.01)
*A61B 6/50* (2024.01)
*H04N 9/03* (2023.01)
*H04N 9/31* (2006.01)

(52) U.S. Cl.
CPC ......... *H04N 9/3188* (2013.01); *H04N 9/3194* (2013.01)

(56) References Cited

U.S. PATENT DOCUMENTS

| | | | | |
|---|---|---|---|---|
| 8,611,491 | B2* | 12/2013 | Holler | A61B 6/0414 378/37 |
| 9,820,705 | B2* | 11/2017 | Kim | G03B 21/208 |
| 9,943,271 | B2* | 4/2018 | Dirauf | G06V 40/28 |
| 9,993,223 | B2* | 6/2018 | Erhard | A61B 6/0414 |
| 10,357,216 | B2* | 7/2019 | Sugiyama | A61B 6/502 |
| 11,317,882 | B2* | 5/2022 | Nakayama | A61B 6/461 |
| 11,534,121 | B2* | 12/2022 | Konno | A61B 6/0414 |
| 11,627,921 | B2* | 4/2023 | Paige | A61B 6/08 378/37 |
| 2009/0225936 | A1* | 9/2009 | Kashiwagi | A61B 6/08 378/98.3 |
| 2009/0299218 | A1 | 12/2009 | Holler et al. | |
| 2010/0054402 | A1* | 3/2010 | Fischer | A61B 6/542 378/37 |
| 2010/0208037 | A1* | 8/2010 | Sendai | A61B 6/463 348/51 |
| 2014/0328458 | A1 | 11/2014 | Erhard et al. | |
| 2015/0351709 | A1* | 12/2015 | Dirauf | A61B 6/0492 378/206 |
| 2016/0135767 | A1* | 5/2016 | Kim | A61B 6/06 378/62 |
| 2017/0172531 | A1 | 6/2017 | Sugiyama et al. | |
| 2020/0253572 | A1 | 8/2020 | Nakayama | |
| 2021/0298696 | A1* | 9/2021 | Paige | A61B 6/0414 |
| 2021/0298702 | A1* | 9/2021 | Konno | A61B 6/502 |
| 2021/0401381 | A1* | 12/2021 | Wells | A61B 6/502 |
| 2022/0087626 | A1* | 3/2022 | Hunsdon | A61B 6/40 |
| 2022/0096024 | A1* | 3/2022 | Fujimoto | A61B 6/0414 |
| 2022/0096025 | A1* | 3/2022 | Fujimoto | A61B 6/0414 |
| 2022/0096026 | A1* | 3/2022 | Fujimoto | A61B 6/08 |
| 2022/0096031 | A1* | 3/2022 | Konno | A61B 6/0492 |
| 2022/0096032 | A1* | 3/2022 | Fujimoto | A61B 6/0492 |
| 2022/0096037 | A1* | 3/2022 | Fujimoto | A61B 6/502 |
| 2022/0096042 | A1* | 3/2022 | Gemma | A61B 6/469 |
| 2022/0101523 | A1* | 3/2022 | Konno | A61B 6/0414 |
| 2022/0101524 | A1* | 3/2022 | Konno | A61B 6/025 |
| 2022/0101529 | A1* | 3/2022 | Komori | A61B 6/0492 |
| 2022/0101553 | A1* | 3/2022 | Konno | A61B 6/0414 |
| 2022/0101571 | A1* | 3/2022 | Konno | A61B 6/502 |
| 2023/0005149 | A1* | 1/2023 | Nakayama | A61B 6/10 |
| 2023/0123188 | A1* | 4/2023 | Paige | A61B 6/463 378/37 |

FOREIGN PATENT DOCUMENTS

| | | |
|---|---|---|
| JP | 2009-285345 A | 12/2009 |
| JP | 2014-533548 A | 12/2014 |
| JP | 2017-113540 A | 6/2017 |
| JP | 2020-127650 A | 8/2020 |
| WO | 2020069031 A1 | 4/2020 |

* cited by examiner

| IDENTIFICATION INFORMATION | PROJECTION SURFACE SIZE INFORMATION | IRRADIATION FIELD |
|---|---|---|
| B001(40A) | 24 × 30 | 24 × 30 |
| B002(40B) | 18 × 24 | 18 × 24 |
| B003(40C) | 10 × 24 | 18 × 24 |
| B004 | 10 × 10 | 9 × 9 |
| ⋮ | ⋮ | ⋮ |

FIG. 11

| PROJECTION DISTANCE D (mm) | MAGNIFICATION M | PROJECTION IMAGE ENLARGEMENT AND REDUCTION RATIO | DISPLAY IMAGE ENLARGEMENT AND REDUCTION RATIO |
|---|---|---|---|
| 0 | - | - | - |
| ⋮ | ⋮ | ⋮ | ⋮ |
| 200 | 0.5 | 1 | 0.5 |
| ⋮ | ⋮ | ⋮ | ⋮ |
| 300(D1) | 0.75 | 1 | 0.75 |
| ⋮ | ⋮ | ⋮ | ⋮ |
| 400(D2) | 1 | 1 | 1 |
| ⋮ | ⋮ | ⋮ | ⋮ |
| 600(D3) | 1.5 | 1 | 1.5 |

FIG. 13

| PROJECTION DISTANCE D (mm) | MAGNIFICATION M | PROJECTION IMAGE ENLARGEMENT AND REDUCTION RATIO | DISPLAY IMAGE ENLARGEMENT AND REDUCTION RATIO |
|---|---|---|---|
| 0 | - | - | - |
| ⋮ | ⋮ | ⋮ | ⋮ |
| 200 | 0.5 | 2 | 1 |
| ⋮ | ⋮ | ⋮ | ⋮ |
| 300 | 0.75 | 1.33 | 1 |
| ⋮ | ⋮ | ⋮ | ⋮ |
| 400 | 1 | 1 | 1 |
| ⋮ | ⋮ | ⋮ | ⋮ |
| 600 | 1.5 | 0.67 | 1 |

FIG. 15

| PROJECTION DISTANCE D (mm) | MAGNIFICATION M | PROJECTION IMAGE ENLARGEMENT AND REDUCTION RATIO | | DISPLAY IMAGE ENLARGEMENT AND REDUCTION RATIO | |
|---|---|---|---|---|---|
| | | GUIDE INFORMATION | IMAGING INFORMATION | GUIDE INFORMATION | IMAGING INFORMATION |
| 0 | - | - | - | - | - |
| ... | ... | ... | ... | ... | ... |
| 200 | 0.5 | 1 | 2 | 0.5 | 1 |
| ... | ... | ... | ... | ... | ... |
| 300 | 0.75 | 1 | 1.33 | 0.75 | 1 |
| ... | ... | ... | ... | ... | ... |
| 400 | 1 | 1 | 1 | 1 | 1 |
| ... | ... | ... | ... | ... | ... |
| 600 | 1.5 | 1 | 0.67 | 1.5 | 1 |

INFORMATION PROCESSING DEVICE, INFORMATION PROCESSING METHOD, AND INFORMATION PROCESSING PROGRAM

CROSS-REFERENCE TO RELATED APPLICATIONS

The present application claims priority under 35 U.S.C. § 119 to Japanese Patent Application No. 2020-166465, filed on Sep. 30, 2020. The above application is hereby expressly incorporated by reference, in its entirety, into the present application.

BACKGROUND

Technical Field

The present disclosure relates to an information processing device, an information processing method, and an information processing program.

Related Art

In the related art, a radiography apparatus is known which performs radiography for the purpose of medical diagnosis. An example of this type of radiography apparatus is a mammography apparatus that captures an image of a breast of a subject. The mammography apparatus irradiates the breast of the subject which is an imaging part with radiation to capture an image in a state in which the breast is compressed by a compression plate.

Further, a technique is known which displays a skin line of the breast on an imaging table in a mammography apparatus (see, for example, JP2008-086389A). JP2008-086389A describes a technique that generates a skin line image of the breast from a radiographic image of the breast in a compressed state and projects the skin line image onto the imaging table in a case in which the image of the breast is captured next time.

In recent years, a technique has been required in which an image projection unit including a projection lens can project various kinds of information including, for example, a skin line image onto a compression plate in a mammography apparatus. In general, the size (so-called screen size) of a display image displayed on the projection surface by the projection of an image by the image projection unit is proportional to the distance from the image projection unit to the projection surface. Therefore, in a case in which the image projection unit is fixed and the compression plate is moved to compress the breast, the distance from the image projection unit to the projection surface of the compression plate changes, and the size of the display image also changes.

Therefore, a technique is required which can project the display image with an appropriate size onto the compression plate even in a case in which the compression plate is moved. For example, it is desirable to display a skin line image with an appropriate size matched with the actual size of the breast on the compression plate and to display characters indicating various kinds of information including compression pressure on the compression plate while keeping the size of the characters constant even in a case in which the compression plate is moved.

SUMMARY

The present disclosure has been made in view of the above-mentioned problems, and an object of the present disclosure is to provide an information processing device, an information processing method, and an information processing program that can display an image with an appropriate size even in a case in which a compression member is moved.

According to a first aspect of the present disclosure, there is provided an information processing device including at least one processor. The processor acquires distance information indicating a projection distance, which is a distance from an image projection unit that projects a projection image onto a projection surface of a compression member to the projection surface, in a mammography apparatus that irradiates a breast compressed by the compression member with radiation to capture a radiographic image, and controls the image projection unit such that the projection image having a size corresponding to the projection distance indicated by the distance information is projected onto the projection surface in a case in which the image projection unit projects the projection image at a magnification corresponding to the projection distance.

According to a second aspect of the present disclosure, in the first aspect, the processor may perform control to project the projection image having the size corresponding to the projection distance indicated by the distance information onto the projection surface such that a size of a display image displayed on the projection surface by the projection of the projection image at the magnification corresponding to the projection distance by the image projection unit is a predetermined size.

According to a third aspect of the present disclosure, in the above aspects, in a case in which an image of the breast as an object to be imaged was captured in the past, the processor may acquire, as the distance information, information indicating the projection distance at a time when the image was captured in the past.

According to a fourth aspect of the present disclosure, in the above aspects, the processor may perform control to sequentially project plural the projection images having different sizes onto the projection surface, following a change in the projection distance indicated by the distance information.

According to a fifth aspect of the present disclosure, in the fourth aspect, the processor may perform control such that, each time an amount of change in the projection distance indicated by the distance information is a predetermined amount, the projection image having the size corresponding to the projection distance indicated by the distance information at that time is projected onto the projection surface.

According to a sixth aspect of the present disclosure, in the above aspects, the processor may acquire projection surface size information indicating a size of the projection surface and perform control to project, onto the projection surface, the projection image having a size that allows the entire projection image to be projected onto the projection surface on the basis of the projection surface size information.

According to a seventh aspect of the present disclosure, in the above aspects, the projection image may include guide information that serves as a guide in a case in which the breast is positioned.

According to an eighth aspect of the present disclosure, in the above aspects, the projection image may include imaging information represented by characters.

According to a ninth aspect of the present disclosure, in the first to sixth aspects, the projection image may include guide information that serves as a guide in a case in which the breast is positioned and imaging information represented by characters, and the processor may perform control to project the imaging information having the size corresponding to the projection distance indicated by the distance information onto the projection surface.

According to a tenth aspect of the present disclosure, in the eighth or ninth aspect, the imaging information may include at least one of information indicating a compression pressure of the breast by the compression member, information indicating a thickness of the breast in a compression direction in which the breast is compressed, subject information indicating a subject pertaining to the breast as an object to be imaged, radiographer information indicating a radiographer who performs imaging, date information indicating a date of imaging, or angle information indicating an angle at which an image of the breast is captured.

According to an eleventh aspect of the present disclosure, in the above aspects, the processor may perform control to stop the projection of the projection image in a case in which the projection distance indicated by the distance information is less than a predetermined threshold value.

According to a twelfth aspect of the present disclosure, in the above aspects, the processor may perform control to project the projection image having the size corresponding to the projection distance indicated by the distance information onto the projection surface in a case in which the projection distance indicated by the distance information is constant for a predetermined period and perform control to stop the projection of the projection image while the projection distance indicated by the distance information is changing.

According to a thirteenth aspect of the present disclosure, there is provided an information processing method including: acquiring distance information indicating a projection distance, which is a distance from an image projection unit that projects a projection image onto a projection surface of a compression member to the projection surface, in a mammography apparatus that irradiates a breast compressed by the compression member with radiation to capture a radiographic image; and controlling the image projection unit such that the projection image having a size corresponding to the projection distance indicated by the distance information is projected onto the projection surface in a case in which the image projection unit projects the projection image at a magnification corresponding to the projection distance.

According to a fourteenth aspect of the present disclosure, there is provided an information processing program that causes a computer to perform a process including: acquiring distance information indicating a projection distance, which is a distance from an image projection unit that projects a projection image onto a projection surface of a compression member to the projection surface, in a mammography apparatus that irradiates a breast compressed by the compression member with radiation to capture a radiographic image; and controlling the image projection unit such that the projection image having a size corresponding to the projection distance indicated by the distance information is projected onto the projection surface in a case in which the image projection unit projects the projection image at a magnification corresponding to the projection distance.

According to the present disclosure, it is possible to display an image with an appropriate size even in a case in which the compression member is moved.

BRIEF DESCRIPTION OF THE DRAWINGS

FIG. 11 is a diagram illustrating a change in the size of the display image according to the projection distance.

FIG. 13 is a diagram illustrating the method for generating the projection image according to the projection distance.

FIG. 15 is a diagram illustrating the method for generating the projection image according to the projection distance.

DETAILED DESCRIPTION

Hereinafter, embodiments of the present disclosure will be described in detail with reference to the drawings. In addition, each of the embodiments does not limit the present disclosure.

First Embodiment

Figure 1:
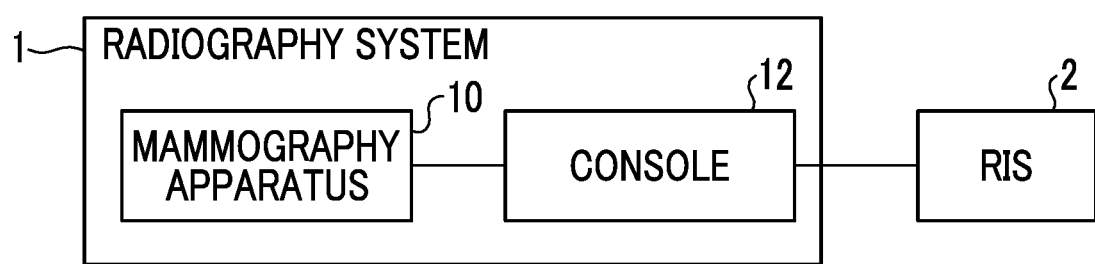
FIG. 1 is a diagram schematically illustrating an example of the overall configuration of a radiography system according to each embodiment.

First, an example of the overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The mammography apparatus 10 according to this embodiment is an example of a radiography apparatus according to the present disclosure. Further, the console 12 according to this embodiment is an example of an information processing device according to the present disclosure.

Figure 2:
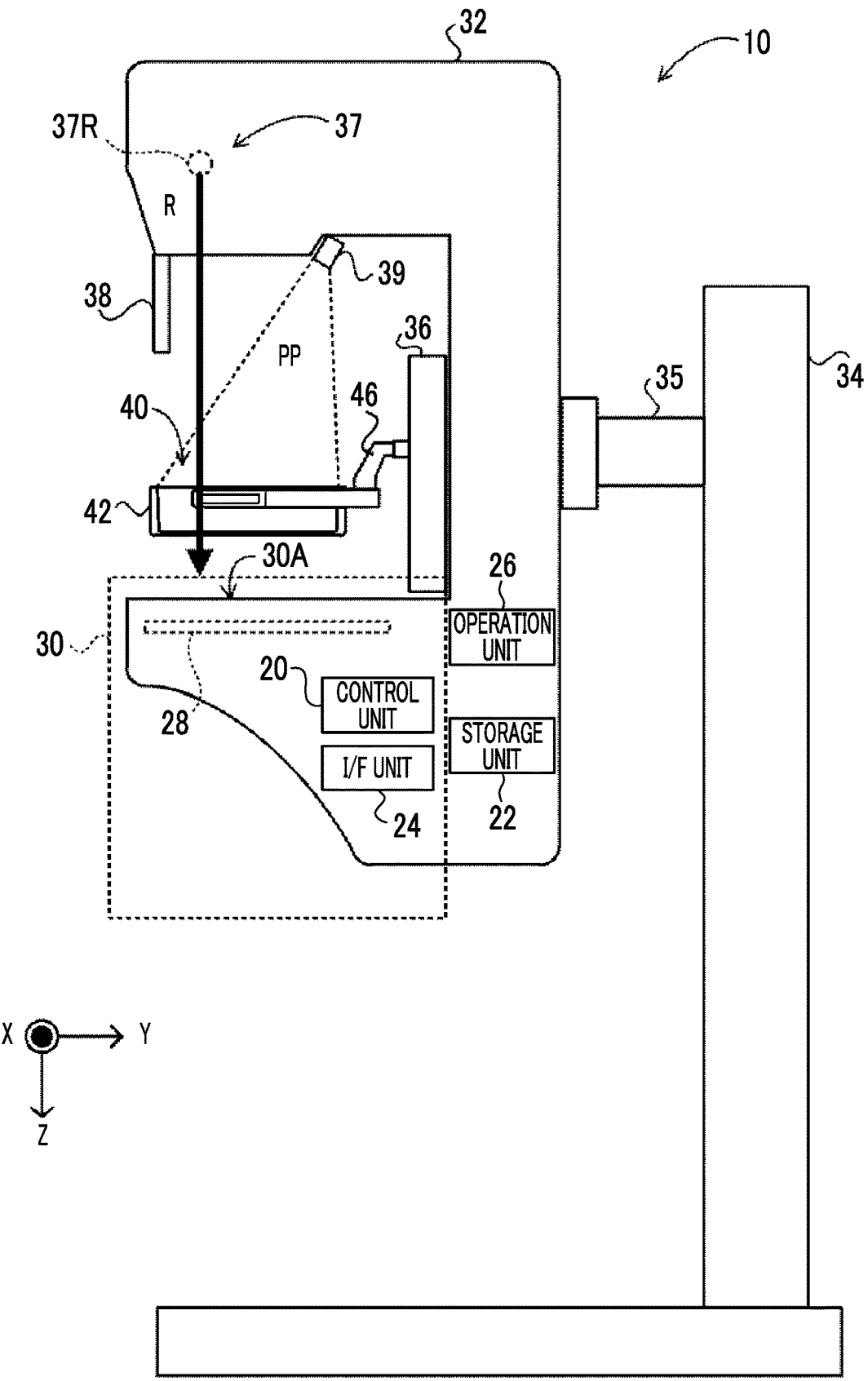
FIG. 2 is a side view illustrating an example of the outward appearance of a mammography apparatus according to each embodiment.

First, the mammography apparatus 10 according to this embodiment will be described. FIG. 2 is a side view illustrating an example of the outward appearance of the mammography apparatus 10 according to this embodiment. In addition, FIG. 2 illustrates an example of the outward appearance of the mammography apparatus 10 as viewed from the right side of a subject.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of a breast of the subject not only in a state in which the subject is standing (standing state) but also in a state in which the subject is sitting, for example, on a chair (including a wheelchair) (sitting state).

As illustrated in FIG. 2, the mammography apparatus 10 according to this embodiment comprises a control unit 20, a storage unit 22, and an interface (I/F) unit 24 which are provided in an imaging table 30. The control unit 20 controls the overall operation of the mammography apparatus 10 under the control of the console 12. The control unit 20 comprises a central processing unit (CPU), a read only memory (ROM), and a random access memory (RAM) which are not illustrated. For example, various programs including an imaging processing program which is executed by the CPU and is used to perform control related to the capture of radiographic images are stored in the ROM in advance. The RAM temporarily stores various kinds of data. For example, image data of the radiographic image captured by a radiation detector 28 and various other kinds of information are stored in the storage unit 22. Examples of the storage unit 22 include a hard disk drive (HDD) and a solid state drive (SSD).

The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

The operation unit 26 is provided as plural switches in, for example, the imaging table 30 of the mammography apparatus 10. Further, the operation unit 26 may be provided as a touch panel switch or may be provided as a foot switch that is operated by a user's feet.

As illustrated in FIG. 2, the radiation detector 28 is disposed in the imaging table 30. In the mammography apparatus 10 according to this embodiment, in a case in which imaging is performed, the breast of the subject is positioned on an imaging surface 30A of the imaging table 30 by a user such as a doctor or a radiology technician. The radiation detector 28 detects the radiation R transmitted through the breast and the imaging table 30, generates a radiographic image on the basis of the detected radiation R, and outputs image data indicating the generated radiographic image. In addition, the type of the radiation detector 28 is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R. As illustrated in FIG. 2, the radiation emitting unit 37 is provided in an arm portion 32 together with the imaging table 30 and a compression unit 36. The radiation emitting unit 37 according to this embodiment is configured such that an irradiation field can be changed. The irradiation field may be changed, for example, by the operation of the operation unit 26 by the user or by the control unit 20 according to the type of an attached compression plate 40.

At least one projector 39, which is an example of an image projection unit according to the present disclosure, is provided at a position of the arm portion 32 which is away from the subject below the radiation emitting unit 37. The projector 39 projects a projection image PP onto a projection surface of the compression plate 40 under the control of the console 12. In a case in which the projection image PP is projected by the projector 39, a display image DP corresponding to the projection image PP is displayed on the projection surface of the compression plate 40. The projection image PP includes at least one of guide information GI or imaging information RI which will be described below. The projection surface is at least one surface that constitutes the compression plate 40. Known projectors, such as a liquid crystal projector, a Digital Light Processing (DLP) (registered trademark) projector, and a laser projector, can be used as the projector 39. In addition, plural projectors 39 that can project the projection image PP onto plural projection surfaces of the compression plate 40 may be provided. Further, for example, a mirror for changing the projection direction of the projector 39 may be provided.

A face guard 38 is attachably and detachably provided at a position of the arm portion 32 which is close to the subject below the radiation emitting unit 37. The face guard 38 is a protective member for protecting the subject from the radiation R emitted from the radiation source 37R.

As illustrated in FIG. 2, the mammography apparatus 10 according to this embodiment comprises the arm portion 32, a base 34, and a shaft portion 35. The arm portion 32 is held by the base 34 so as to be movable in an up-down direction (Z-axis direction). The shaft portion 35 connects the arm portion 32 to the base 34. In addition, the arm portion 32 can be relatively rotated with respect to the base 34, using the shaft portion 35 as a rotation axis.

Each of the arm portion 32, the imaging table 30, and the compression unit 36 can be relatively rotated with respect to the base 34, using the shaft portion 35 as a rotation axis. In this embodiment, engagement portions (not illustrated) are provided in each of the base 34, the arm portion 32, the imaging table 30, and the compression unit 36. The state of the engagement portions is switched to connect each of the arm portion 32, the imaging table 30, and the compression unit 36 to the base 34. The arm portion 32, the imaging table 30, and the compression unit 36 connected to the shaft portion 35 are integrally rotated on the shaft portion 35.

The compression unit 36 is provided with a compression plate driving unit (not illustrated) that moves the compression plate 40 in the up-down direction (Z-axis direction). The compression plate 40 according to this embodiment has a function of compressing the breast of the subject. A support portion 46 of the compression plate 40 is detachably attached to the compression plate driving unit and is moved in the up-down direction (Z-axis direction) by the compression plate driving unit to compress the breast of the subject between the compression plate 40 and the imaging table 30. The compression plate 40 according to this embodiment is an example of a compression member according to the present disclosure.

There are plural types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 for so-called spot imaging that captures a radiographic image of only the region in which a lesion is present is known. Further, other types of compression plates 40 include, for example, a compression plate corresponding to the size of the breast, a compression plate for axillary imaging, and a compression plate for enlargement imaging.

As a specific example, three types of compression plates 40A to 40C that can be attached to the mammography apparatus 10 according to this embodiment will be described with reference to FIGS. 3 to 5, respectively. Hereinafter, in a case in which the compression plates 40A to 40C are generically referred to regardless of the type, they are simply referred to as "compression plates 40".

Figure 3:
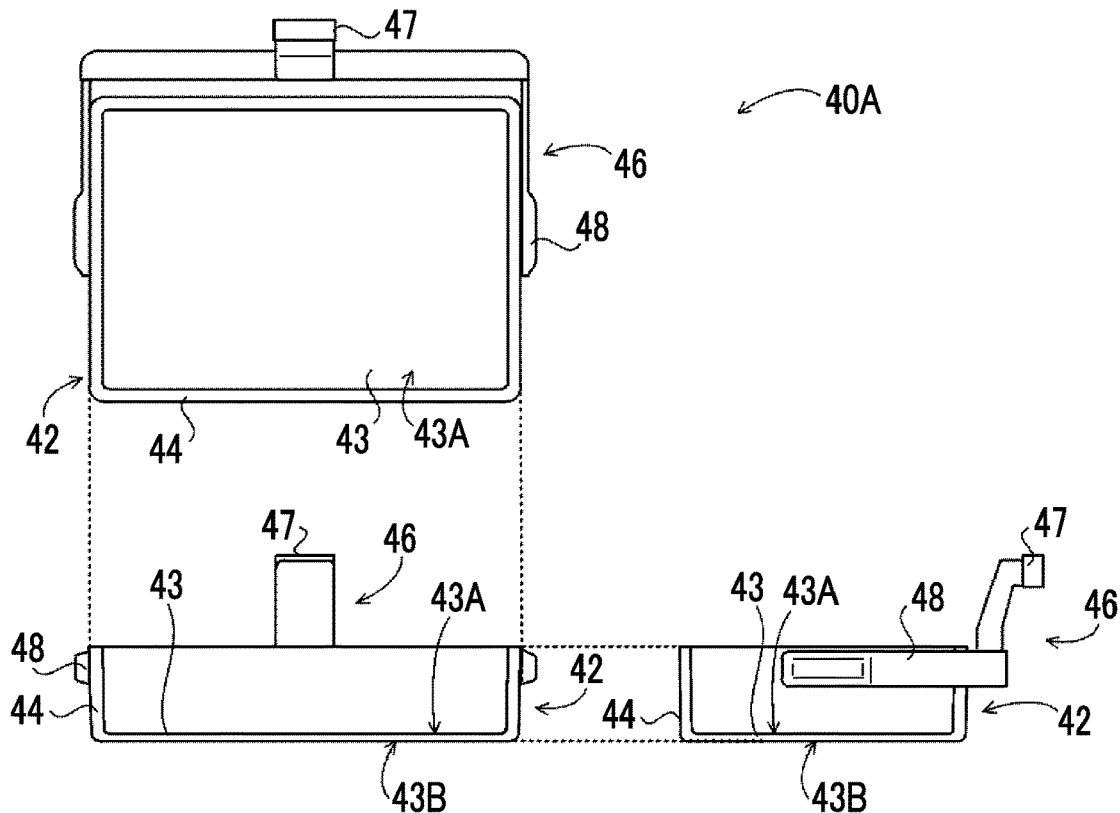
FIG. 3 is a three-view diagram illustrating an example of a compression plate.

FIG. 3 is a three-view diagram illustrating an example of the compression plate 40A according to this embodiment. The compression plate 40A is a standard-size compression plate that is mainly used outside Japan. The three-view diagram illustrated in FIG. 3 includes a plan view (top view) of the compression plate 40A viewed from the upper side (from the radiation emitting unit 37), a side view of the compression plate 40A viewed from the subject, and a side view of the compression plate 40A viewed from the right side of the subject. As illustrated in FIG. 3, the compression plate 40A according to this embodiment includes a compression portion 42 and a support portion 46.

The compression portion 42 is formed in a concave shape in a cross-sectional view in which a bottom portion 43 is surrounded by a wall portion 44. In the bottom portion 43, the thickness of a plate having a contact surface 43B that comes into contact with the breast of the subject is substantially constant, and an upper surface 43A that faces the radiation source 37R is flat and has a substantially uniform height. Further, the wall portion 44 is relatively high and has a substantially uniform height.

It is preferable that the compression portion 42 is optically transparent in order to check positioning or a compressed state in the compression of the breast. In addition, the compression portion 42 is made of a material having high transmittance for the radiation R. Specific examples of the material are resins, such as polycarbonate (PC), polyethylene terephthalate (PET), acrylic, and polypropylene (PP). However, the material is not particularly limited.

The support portion 46 is an example of a support member according to the present disclosure and includes an attachment portion 47 and an arm 48. The attachment portion 47 has a function of attaching the compression plate 40 to the mammography apparatus 10, specifically, the compression plate driving unit in the compression plate 40. The arm 48 has a function of supporting the compression portion 42.

Figure 4:
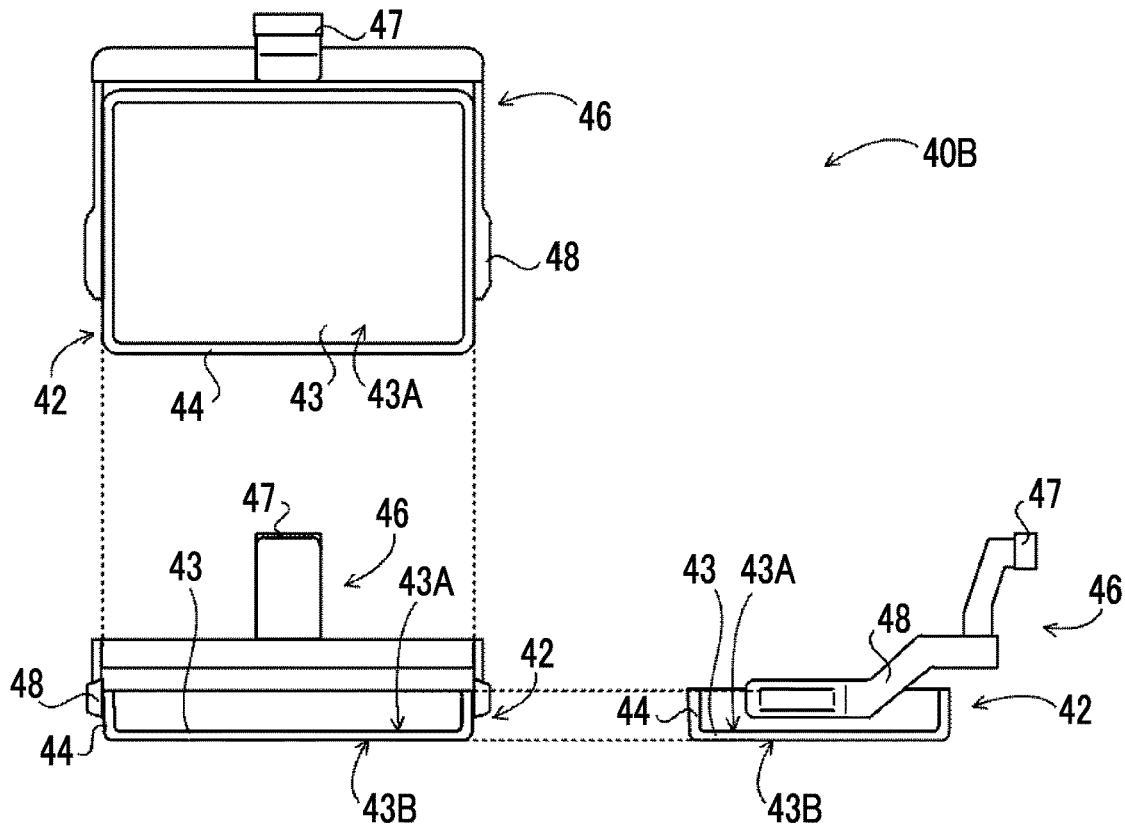
FIG. 4 is a three-view diagram illustrating an example of a compression plate.

FIG. 4 is a three-view diagram illustrating an example of the compression plate 40B according to this embodiment. The compression plate 40B is a compression plate having a smaller size than the compression plate 40A that is mainly used in Japan and is suitable for Japanese people who tend to have smaller breasts than foreigners. The three-view diagram illustrated in FIG. 4 includes a plan view (top view) of the compression plate 40B viewed from the upper side (from the radiation emitting unit 37), a side view of the compression plate 40B viewed from the subject, and a side view of the compression plate 40B viewed from the right side of the subject. As illustrated in FIG. 4, the compression plate 40B according to this embodiment includes a compression portion 42 and a support portion 46, similarly to the compression plate 40A. The compression plate 40B has a smaller bottom portion 43 and a lower wall portion 44 than the compression plate 40A illustrated in FIG. 3. Further, the support portion 46 includes an arm 48 having a different shape. The other configurations are the same as those of the compression plate 40A.

Figure 5:
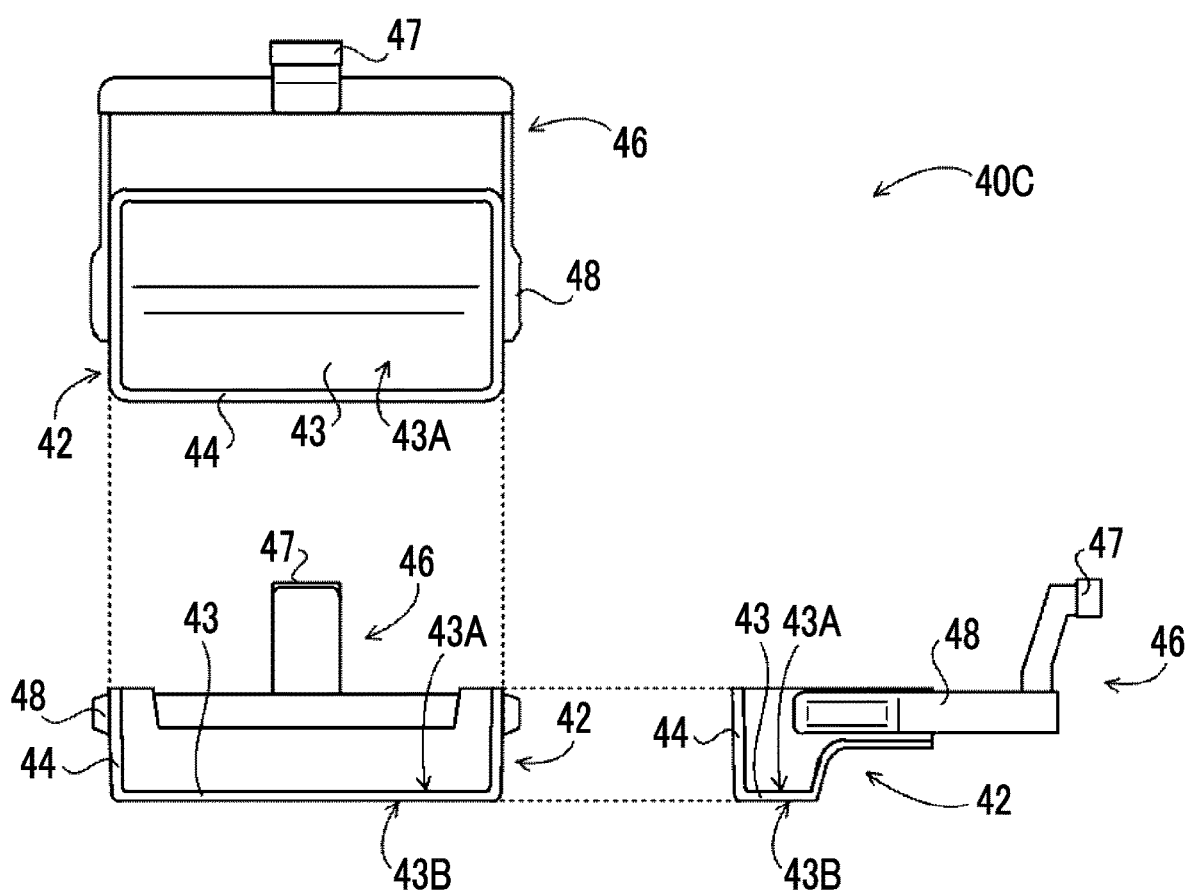
FIG. 5 is a three-view diagram illustrating an example of a compression plate.

FIG. 5 is a three-view diagram illustrating an example of the compression plate 40C according to this embodiment. The compression plate 40C is a compression plate for a small breast and has a shape that makes it easy for a radiographer to position and compress the breast. The three-view diagram illustrated in FIG. 5 includes a plan view (top view) of the compression plate 40C viewed from the upper side (from the radiation emitting unit 37), a side view of the compression plate 40C viewed from the subject, and a side view of the compression plate 40C viewed from the right side of the subject. As illustrated in FIG. 5, the compression plate 40C according to this embodiment includes a compression portion 42 and a support portion 46, similarly to the compression plates 40A and 40B. The compression plate 40C includes a bottom portion 43 which is not flat and in which a part close to an attachment portion 47 is higher than a part close to the chest wall (a part away from the attachment portion 47). Further, the height of a wall portion 44 is not uniform. In the wall portion 44, the height of a part close to the chest wall is lower than the height of the other parts.

In accordance with the above, different types of compression plates 40 are prepared according to, for example, the physique of the subject (for example, the size of the breast) and the type of imaging (for example, enlargement imaging and spot imaging) and can be attached to and detached from the mammography apparatus 10. Therefore, the mammography apparatus 10 according to this embodiment acquires identification information for identifying the type of the compression plate 40.

For example, plural pins whose disposition varies depending on the type of the compression plate 40 may be provided as the identification information in the attachment portion 47 of the compression plate 40, and the identification information may be read by a sensor that can detect the disposition of the pins provided in the mammography apparatus 10. In addition, for example, a detection marker corresponding to the type of the compression plate 40 may be provided as identification information at any position of the compression plate 40, and the identification information may be read by a sensor such as a photointerrupter that can detect each bit of the detection marker provided in the mammography apparatus 10. Further, for example, the mammography apparatus 10 may store a table, in which the identification information and weight of the compression plate 40 are associated with each other, in the storage unit 22 in advance, and the weight of the compression plate 40 measured by a sensor that can detect the weight may be collated with the table to acquire the identification information.

Next, the console 12 according to this embodiment will be described. The console 12 has a function of controlling the mammography apparatus 10 using, for example, an imaging order and various kinds of information acquired from a radiology information system (RIS) 2 through a wireless local area network (LAN) or the like and instructions input by the user through an operation unit 56 or the like.

The imaging order includes, for example, subject information, such as the name, sex, and date of birth of the subject whose image is to be captured, and an imaging item to be captured. For example, the imaging item is the designation of various types of imaging, such as cranio-caudal (CC) imaging, medio-lateral oblique (MLO) imaging, enlargement imaging, and spot imaging, for each of the left and right breasts.

Figure 6:
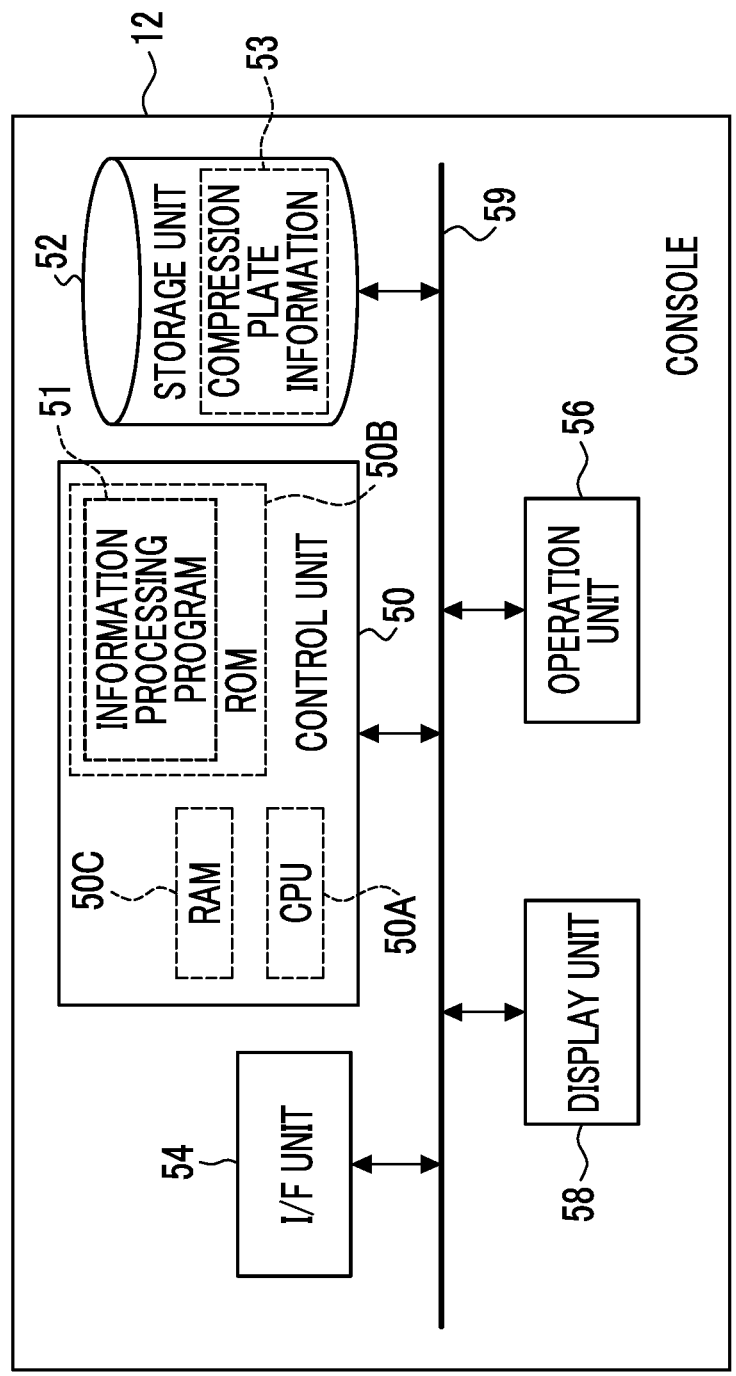
FIG. 6 is a block diagram illustrating an example of the hardware configuration of a console according to each embodiment.

For example, the console 12 according to this embodiment is a server computer. As illustrated in FIG. 6, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including an information processing program 51 (which will be described below) executed by the CPU 50A are stored in the ROM 50B in advance. The RAM 50C temporarily stores various kinds of data. The CPU 50A according to this embodiment is an example of a processor according to the present disclosure, and the ROM 50B according to this embodiment is an example of a memory according to the present disclosure.

For example, the image data of the radiographic image captured by the mammography apparatus 10, compression plate information 53, and various other kinds of information are stored in the storage unit 52. An HDD or an SSD is given as a specific example of the storage unit 52. The image data of the radiographic image is stored so as to be associated with the imaging order.

In addition, imaging information is given to the image data of the radiographic image. For example, the imaging information is at least one of subject information indicating the subject pertaining to the breast as an object to be imaged, radiographer information indicating the radiographer who performs imaging, date information indicating the date of imaging, radiographic image size information indicating the size of the radiographic image, or angle information indicating the angle at which the image of the breast is captured. The radiographer is, for example, a user such as a doctor or a radiology technician. The angle at which the image of the breast is captured is represented by, for example, the rotation angle of the arm portion 32 with respect to the base 34, is 0 degrees in the case of CC imaging, and is equal to or greater than 45 degrees and less than 90 degrees in the case of MLO imaging.

Figures 7, 8:
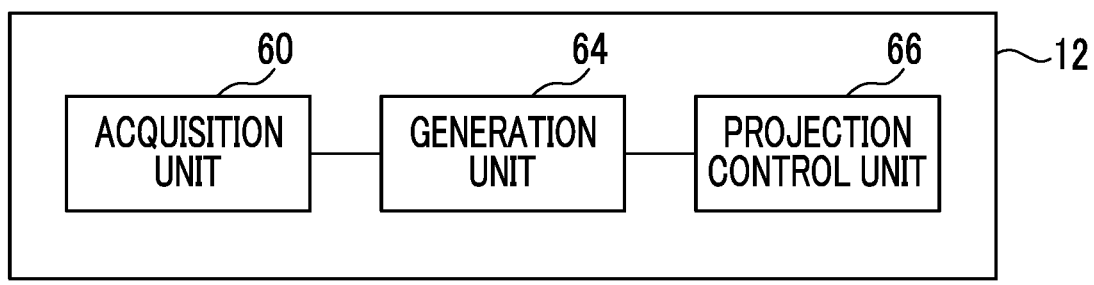
FIG. 7 is a diagram illustrating an example of compression plate information according to each embodiment.
FIG. 8 is a functional block diagram illustrating an example of the functions of the console according to each embodiment.

FIG. 7 illustrates an example of the compression plate information 53. As illustrated in FIG. 7, the compression plate information 53 includes identification information assigned to each type of compression plate 40, information related to the size of the projection surface of the compression plate 40 (hereinafter, referred to as "projection surface size information"), and the size of the irradiation field suitable for the compression plate 40 which are associated with each other. In FIG. 7, the reference numerals of the corresponding compression plates 40A to 40C are also written in an identification information field.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 9:
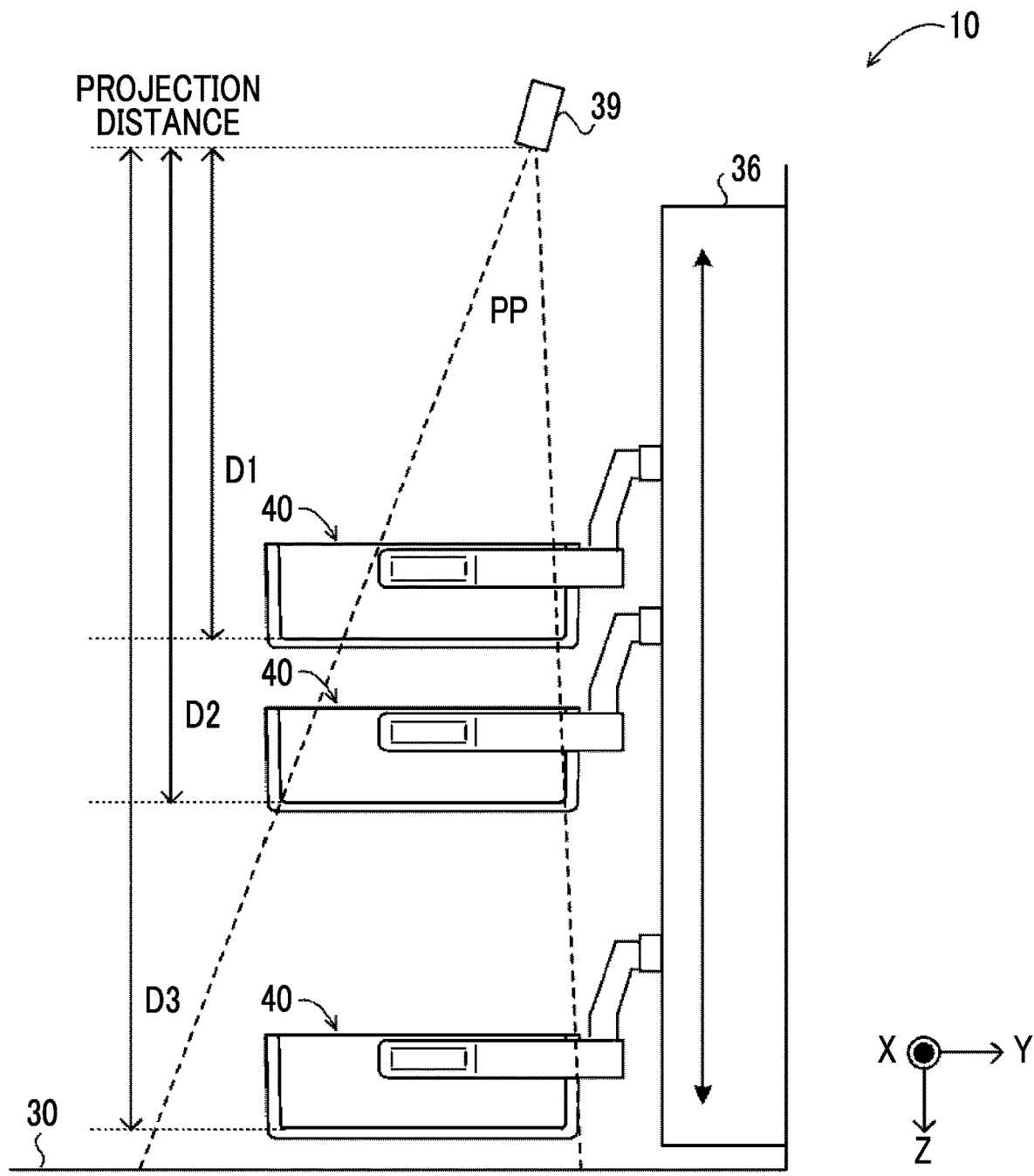
FIG. 9 is a diagram illustrating a change in the size of a display image according to a projection distance.

The size (so-called screen size) of the display image DP displayed on the projection surface of the compression plate 40 in a case in which the projection image PP is projected by the projector 39 will be described with reference to FIGS. 9 to 11. FIG. 9 is a diagram schematically illustrating a state in which the compression plate 40 is disposed at each position where the distance (hereinafter, referred to as a "projection distance D") from the projector 39 to the projection surface of the compression plate 40 is D1 to D3 (D1<D2<D3 in ascending order) in the mammography apparatus 10. As described above, the compression plate 40 is configured to be movable in the up-down direction (Z-axis direction) by the compression plate driving unit provided in the compression unit 36 in order to compress the breast of the subject between the compression plate 40 and the imaging table 30.

As represented by a broken line in FIG. 9, the projection image PP projected from the projector 39 becomes more enlarged as the projection distance D becomes longer due to the optical properties. That is, the projector 39 projects the projection image PP at a magnification M corresponding to the projection distance D. The magnification M is represented by the following Mathematical Expression (1) in a case in which a reference projection distance is Dr and a projection distance for calculating the magnification is D. As can be seen from Mathematical Expression (1), the magnification M is proportional to the projection distance D.

$$M = D/Dr \tag{1}$$

For example, assuming that the reference projection distance Dr at which the magnification M is 1 is D2 (=400 mm), the magnification M in a case in which the projection distance is D1 (=300 mm) is 0.75, and the magnification M in a case in which the projection distance is D3 (=600 mm) is 1.5.

Figure 10:
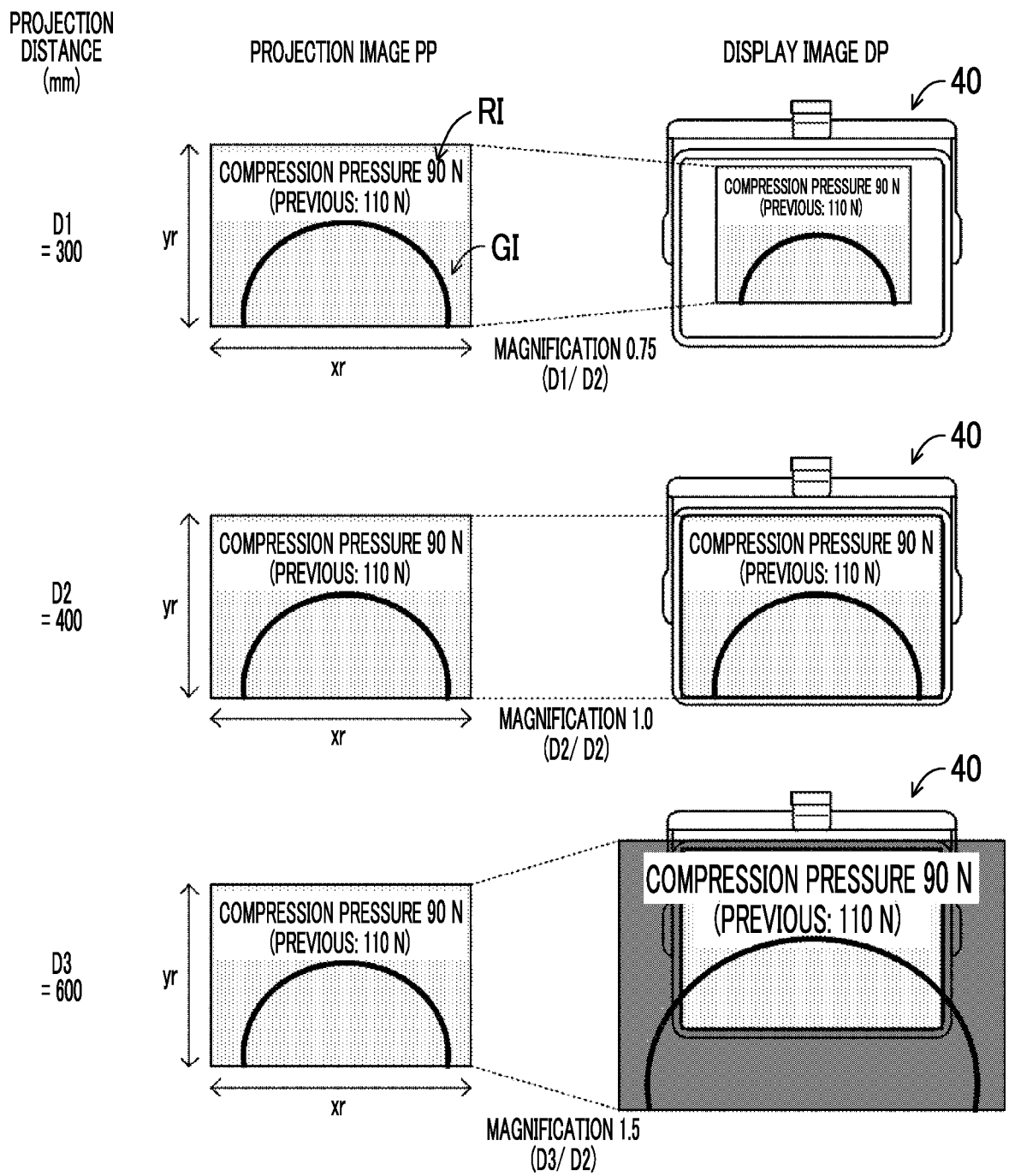
FIG. 10 is a diagram illustrating a change in the size of the display image according to the projection distance.

FIG. 10 is a diagram schematically illustrating the display image DP displayed by the projection of the projection image PP, which has a constant size regardless of the projection distance D, onto the projection surface of the compression plate 40 by the projector 39. FIG. 11 is a table that summarizes the magnification M of the projector 39, the enlargement and reduction ratio of the projection image PP, and the enlargement and reduction ratio of the display image DP for each projection distance D corresponding to FIG. 10. In addition, the enlargement and reduction ratio means an enlargement ratio and a reduction ratio and indicates a ratio with respect to the size of the projection image PP and the size of the display image DP at the reference projection distance Dr at which the magnification M is 1.

The enlargement and reduction ratio of the display image DP is a value obtained by multiplying the enlargement and reduction ratio of the projection image PP by the magnification M corresponding to the projection distance D. Therefore, as illustrated in FIGS. 10 and 11, in a case in which the projection distance D is changed while the size (enlargement and reduction ratio) of the projection image PP is kept constant, the size (enlargement and reduction ratio) of the display image DP also changes according to the change in the projection distance D. That is, in a case in which the projector 39 is fixed and the compression plate 40 is moved in the up-down direction in order to compress the breast while the size (enlargement and reduction ratio) of the projection image PP is kept constant, the projection distance D changes, and the size of the display image DP also changes. In addition, as illustrated in the state in which the projection distance is D3 in FIG. 10, the display image DP may protrude from the projection surface of the compression plate 40. In this case, the display image DP is displayed on the imaging table 30.

As described above, the projection image PP according to this embodiment includes at least one of the guide information GI or the imaging information RI. The guide information GI is information that serves as a guide in a case in which the breast is positioned, and is required to be displayed as the display image DP having an appropriate size matched with the actual size of the breast. Further, the imaging information RI is information represented by characters and is required to be displayed in characters with a constant size for readability even in a case in which the compression plate 40 is moved in the up-down direction. In other words, both the guide information GI and the imaging information RI need to be set such that the apparent size of the display image DP on the projection surface of the compression plate 40 is constant even in a case in which the compression plate 40 is moved in the up-down direction.

Therefore, the console 12 according to this embodiment has a function of controlling the size of the projection image PP according to the projection distance D in order to make the apparent size of the display image DP on the projection surface of the compression plate 40 constant even in a case in which the compression plate 40 is moved in the up-down direction. FIG. 8 is a functional block diagram illustrating an example of the configuration of the console 12 according to this embodiment. As illustrated in FIG. 8, the console 12 comprises an acquisition unit 60, a generation unit 64, and a projection control unit 66. In the console 12 according to this embodiment, the CPU 50A of the control unit 50 executes the information processing program 51 stored in the ROM 50B to function as the acquisition unit 60, the generation unit 64, and the projection control unit 66.

The acquisition unit 60 acquires at least one of the guide information GI or the imaging information RI as information projected onto the projection surface of the compression plate 40 by the projector 39. The guide information GI is information that serves as a guide in a case in which the breast is positioned. Specifically, the guide information GI may be a skin line image (see FIG. 10) indicating at least a portion of the periphery of the breast in the compressed state, an image indicating the position of the nipples, or the captured radiographic image of the breast in the compressed state.

In addition, a unit and method for generating the guide information GI is not particularly limited. For example, the guide information GI may be generated by the console 12, the mammography apparatus 10, or an external device on the basis of the radiographic image of the breast captured in the past. Further, for example, the guide information GI may be a skin line image generated by dividing a radiographic image into a breast region and a blank region on the basis of the density of each pixel of the radiographic image and connecting the pixels which are the boundary points between the breast region and the blank region (see JP2010-051456A).

The imaging information RI is various kinds of information related to the capture of the image of the breast and is represented by characters. Specifically, the imaging information RI is information including at least one of information indicating the compression pressure of the breast by the compression plate 40, information indicating the thickness of the breast in a compression direction in which the breast is compressed, subject information indicating the subject pertaining to the breast as an object to be imaged, radiographer information indicating the radiographer who performs imaging, date information indicating the date of imaging, or angle information indicating the angle at which the image of the breast is captured. In addition, the imaging information RI may be information related to the current imaging or information related to the past imaging. For example, the imaging information RI may include both the compression pressure in the past imaging ("previous: 110N" in FIG. 10) and the currently measured compression pressure ("90N" in FIG. 10) for the same subject.

In addition, the acquisition unit 60 acquires distance information indicating the projection distance D. A unit for acquiring the distance information is not particularly limited. For example, the compression unit 36 may be provided with a sensor that detects the amount of movement of the compression plate driving unit and may detect the amount of movement from a reference position to acquire the distance information. For example, a device that measures the distance to an object to be imaged, such as a time-of-flight (TOF) camera, may be used. Specifically, the TOF camera is a camera that captures a distance image using a TOF method, irradiates an object to be imaged with light, such as infrared rays, and measures the distance between the TOF camera and the object to be imaged on the basis of the time until reflected light is received or a phase change between the emitted light and the received light. In the distance image captured by the TOF camera, each pixel has distance information indicating the distance between the TOF camera and the object to be imaged. Therefore, the distance information of the pixels corresponding to the projection surface of the compression plate 40 may be acquired as the distance information indicating the projection distance D.

The generation unit 64 generates the projection image PP having a size corresponding to the projection distance D indicated by the distance information acquired by the acquisition unit 60. Specifically, the generation unit 64 generates the projection image PP having a size corresponding to the projection distance D indicated by the distance information such that the size of the display image DP displayed on the projection surface by the projection of the projection image PP at the magnification M corresponding to the projection distance D by the projector 39 is a predetermined size.

Here, the predetermined size may be, for example, a size that corresponds to the size of the projection surface and is predetermined for each type of the compression plate 40. The generation unit 64 generates the projection image PP having a size at which the entire projection image PP can be projected according to the size of the projection surface. That is, the generation unit 64 generates the projection image PP having a size at which the display image DP does not protrude from the projection surface of the compression plate 40. In addition, for example, the acquisition unit 60 can acquire the projection surface size information indicating the size of the projection surface to detect the size of the projection surface. Specifically, the acquisition unit 60 acquires the identification information of the compression plate 40 identified by the mammography apparatus 10, collates the identification information with the compression plate information 53 (see FIG. 7) in the storage unit 52, and acquires the projection surface size information corresponding to the compression plate 40 attached to the mammography apparatus 10.

The projection control unit 66 performs control to direct the projector 39 to project the projection image PP, which has been generated by the generation unit 64 and has a size corresponding to the projection distance D indicated by the distance information, onto the projection surface of the compression plate 40. Further, it is desirable that the projection control unit 66 performs control to stop the projection of the projection image PP in a case in which the projection distance D indicated by the distance information is less than a predetermined threshold value. The reason is that, in a case in which the projection distance D is too short, the display image DP displayed on the compression plate 40 is too small to be visually recognized even though the projection image PP is projected.

Figure 12:
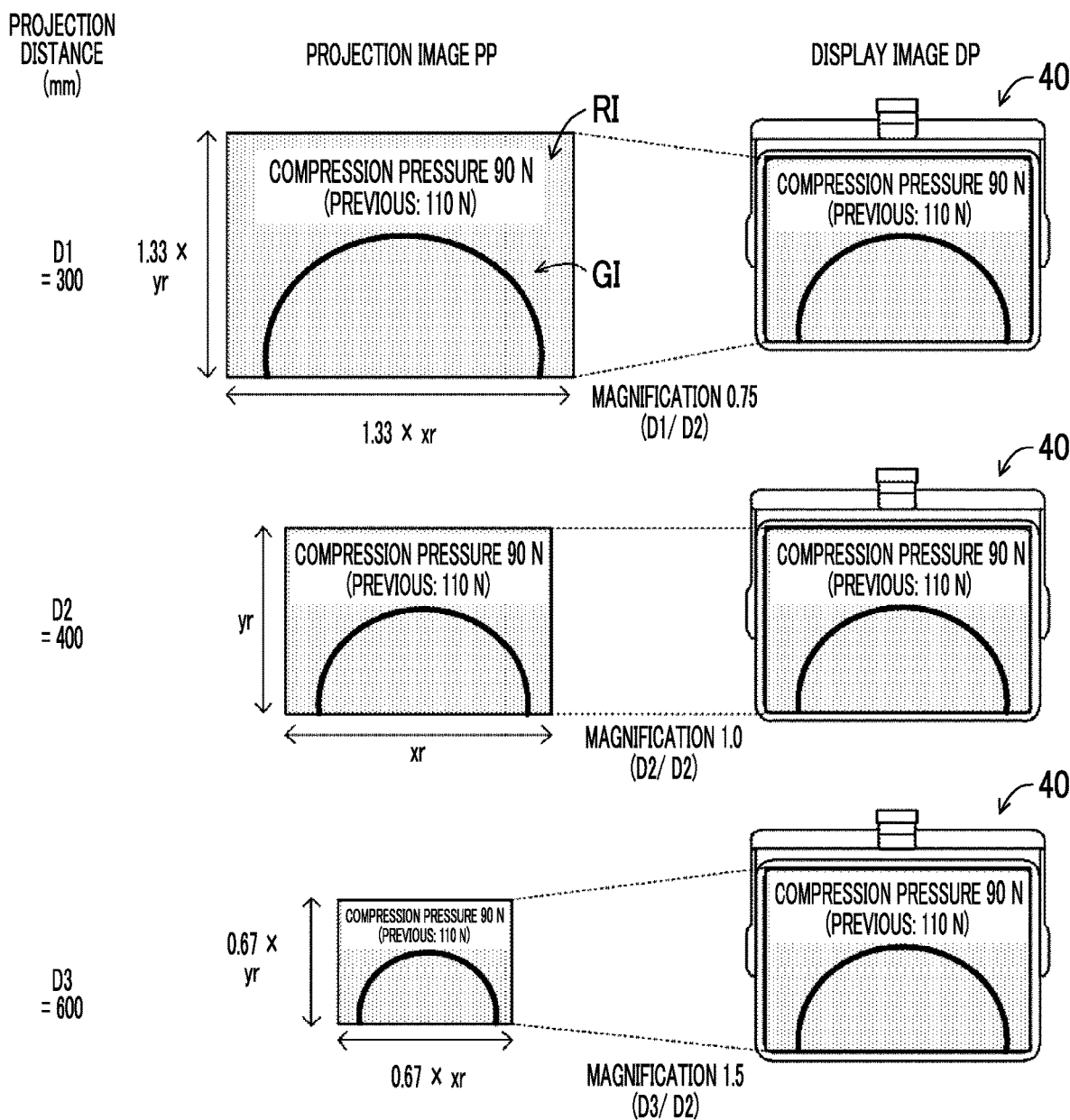
FIG. 12 is a diagram illustrating a method for generating a projection image according to the projection distance.

A specific example of the process of the generation unit 64 and the projection control unit 66 will be described with reference to FIGS. 12 and 13. FIG. 12 is a diagram schematically illustrating the display image DP displayed in a case in which the projector 39 projects the projection image PP with a size corresponding to the projection distance D onto the projection surface of the compression plate 40 at each of the positions where the projection distances are D1 to D3. FIG. 13 is a table that summarizes the magnification M of the projector 39, the enlargement and reduction ratio of the projection image PP, and the enlargement and reduction ratio of the display image DP for each projection distance D corresponding to FIG. 12.

As described above, the enlargement and reduction ratio of the display image DP is a value obtained by multiplying the enlargement and reduction ratio of the projection image PP by the magnification M. Therefore, in a case in which the projection image PP is enlarged or reduced (1/M) times in advance according to the magnification M for each projection distance D, it is possible to keep the size (enlargement and reduction ratio) of the display image DP constant even though the projection distance D changes. In a case in which the horizontal width of the projection image PP at the reference projection distance Dr is xr, the horizontal width x of the projection image PP at the projection distance D is represented by the following Mathematical Expression (2). In a case in which the vertical width of the projection image PP at the reference projection distance Dr is yr, the vertical width y of the projection image PP at the projection distance D is represented by the following Mathematical Expression (3).

$$x=(1/M) \times xr \qquad (2)$$

$$y=(1/M) \times yr \qquad (3)$$

As illustrated in FIGS. 12 and 13, for example, in a case in which the projection distance is D1 (=300 mm) and the magnification M is 0.75, the generation unit 64 enlarges the projection image PP 1.33 times in advance. The projection control unit 66 controls the projector 39 such that the projection image PP enlarged 1.33 times is projected onto the projection surface of the compression plate 40. Therefore, the display image DP having an enlargement and reduction ratio of 1, that is, the display image DP having the same size as that in a case in which the projection distance is D2 (=400 mm) is displayed on the projection surface of the compression plate 40. In addition, in a case in which the projection image PP is enlarged, the size of the projection image PP may be greater than the maximum size of the projection image PP that can be projected by the projector 39. In this case, control may be performed such that a portion of the projection image PP enlarged 1.33 times is cut and the projection image PP is projected onto the compression plate 40.

In addition, for example, in a case in which the projection distance is D3 (=600 mm) and the magnification M is 1.5, the generation unit 64 reduces the projection image PP to 0.67 times in advance. The projection control unit 66 controls the projector 39 such that the projection image PP reduced to 0.67 times is projected onto the projection surface of the compression plate 40. Therefore, the display image DP having an enlargement and reduction ratio of 1, that is, the display image DP having the same size as that in a case in which the projection distance is D2 (=400 mm) is displayed on the projection surface of the compression plate 40.

In addition, the generation unit 64 may calculate the enlargement and reduction ratio of the projection image PP at any time on the basis of Mathematical Expressions (1) to (3). Alternatively, the generation unit 64 may store a table of the enlargement and reduction ratio of the projection image PP corresponding to the projection distance D illustrated in FIG. 13 in the storage unit 52 in advance and refer to the table.

Further, in one mammography operation, the number of times the size of the projection image PP is changed according to the distance information and the timing of the change are not particularly limited. For example, the console 12 may perform control to sequentially project plural projection images PP having different sizes onto the projection surface, following a change in the projection distance D indicated by the distance information. In this case, the acquisition unit 60 acquires the distance information at any time. The generation unit 64 generates the projection image PP having a size corresponding to the projection distance D whenever the projection distance D indicated by the distance information changes. The projection control unit 66 performs control to sequentially project plural projection images PP having different sizes for each projection distance D, following a change in the projection distance D. According to this aspect, in one mammography operation, the size of the display image DP can be kept constant from the positioning of the breast to the completion of imaging. Therefore, it is possible to improve the visibility of the display image DP.

Further, for example, each time the amount of change in the projection distance D indicated by the distance information is a predetermined amount, the console 12 may perform control to project, onto the projection surface, the projection image PP having a size corresponding to the projection distance D indicated by the distance information at that time. For example, the generation unit 64 may generate the projection image PP having a size corresponding to the projection distance D whenever the projection distance D indicated by the distance information changes by 5 mm. The projection control unit 66 performs control to sequentially project plural projection images PP having different sizes for each projection distance D whenever the projection distance D changes by 5 mm. According to this aspect, it is possible to suppress the flickering of the display image DP that is likely to occur due to the frequent switching of the size of the projection image PP.

Further, for example, in a case in which the projection distance D indicated by the distance information is constant for a predetermined period, the console 12 may perform control to project the projection image PP having a size corresponding to the projection distance D indicated by the distance information onto the projection surface. For example, in a case in which the projection distance D indicated by the distance information is constant for a period of 2 seconds or more, the generation unit 64 may generate the projection image PP having a size corresponding to the projection distance D for the period. The projection control unit 66 performs control to project the projection image PP in a case in which the projection distance D is constant for a period of 2 seconds or more. In addition, in this case, the projection control unit 66 may perform control to stop the projection of the projection image PP while the projection distance D indicated by the distance information changes (that is, in a case in which the projection distance D changes within a predetermined period). According to this, it is possible to suppress the flickering of the display image DP due to the frequent switching of the size of the projection image PP.

Further, for example, in a case in which the projection distance D suitable for the breast as the object to be imaged is known in advance, the acquisition unit 60 may acquire the distance information indicating the projection distance D. For example, in a case in which the image of the breast as the object to be imaged was captured in the past, the acquisition unit 60 may acquire, as the distance information, information indicating the projection distance D at the time when the image was captured in the past. Furthermore, for example, in a case in which the images of the left and right breasts of the same subject are continuously captured, the acquisition unit 60 may acquire distance information indicating the projection distance D at the time of imaging related to one of the breasts, whose image has been captured, as distance information related to the other breast whose image is to be captured later. In addition, distance information indicating the average projection distance D of the breasts having similar properties such as the size and softness of the breast may be used. Since the projection image PP having a size corresponding to the projection distance D suitable for the breast as the object to be imaged is projected, it is possible to display the display image DP having an appropriate size.

Further, the console 12 may change, for example, the hue, saturation, brightness, and luminance of the projection image PP according to the projection distance D indicated by the distance information. As the projection distance D becomes longer, the lightness of the display image DP becomes lower due to the optical properties of the projector 39. Therefore, for example, the generation unit 64 may adjust, for example, the hue, saturation, brightness, and luminance of the projection image PP to compensate for the lightness of the display image DP which is lowered according to the projection distance D such that, as the projection distance D becomes longer, the color becomes brighter.

Figure 14:
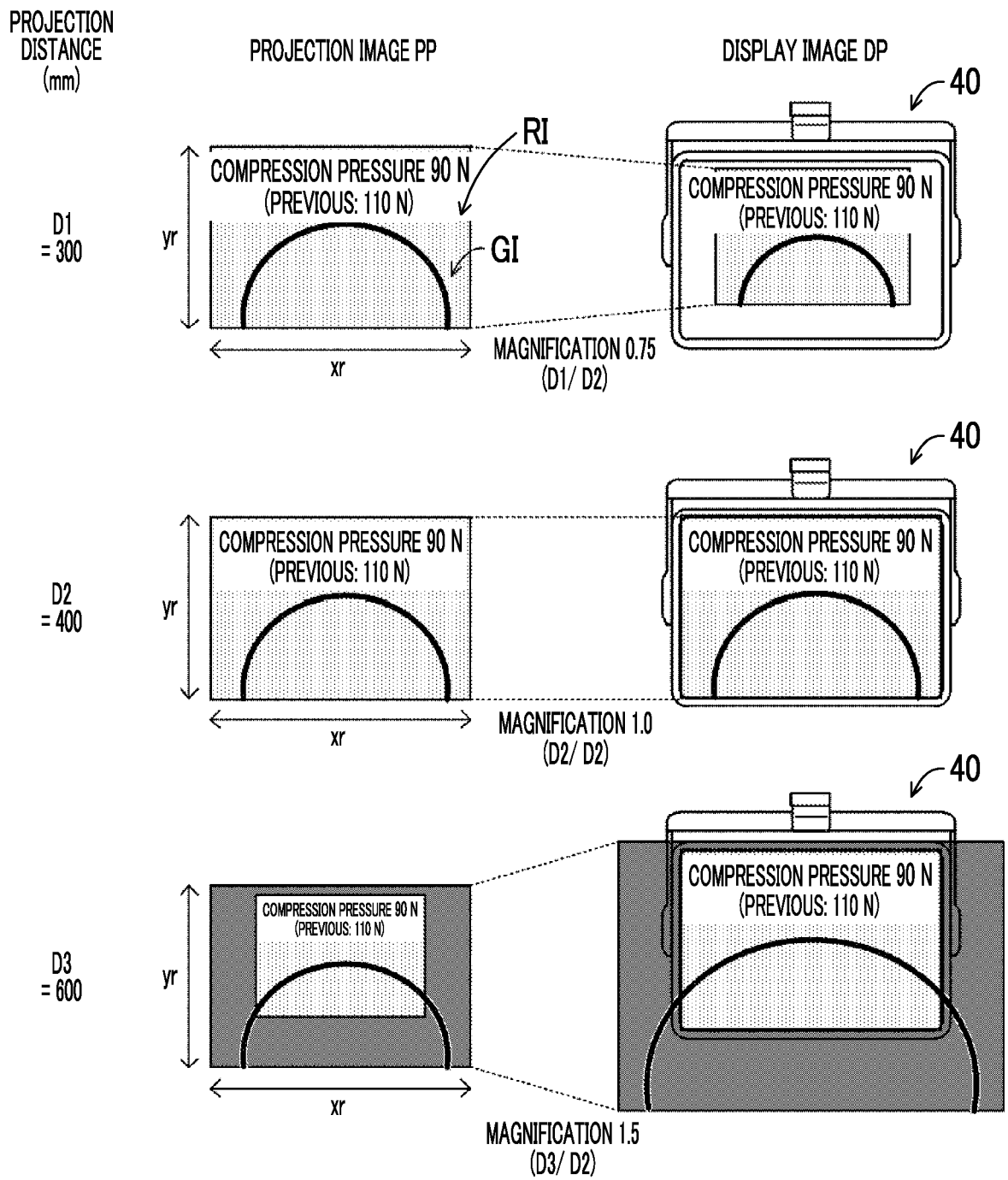
FIG. 14 is a diagram illustrating the method for generating the projection image according to the projection distance.

Furthermore, in a case in which the generation unit 64 generates the projection image PP including the guide information GI and the imaging information RI, the guide information GI and the imaging information RI may be set to have different enlargement and reduction ratios. A specific example of the process of the generation unit 64 and the projection control unit 66 in this case will be described with reference to FIGS. 14 and 15. FIG. 14 is a diagram schematically illustrating the display image DP displayed by the projection of the projection images PP with different sizes (enlargement and reduction ratios) in the guide information GI and the imaging information RI onto the projection surface of the compression plate 40 by the projector 39 at each position where the projection distance is D1 to D3. FIG. 15 illustrates a table that summarizes the magnification M of the projector 39, the enlargement and reduction ratios of the guide information GI and the imaging information RI included in the projection image PP, and the enlargement and reduction ratios of the guide information GI and the imaging information RI included in the display image DP for each projection distance D corresponding to FIG. 14.

For example, for the guide information GI, it is considered that the display image DP may be preferably displayed such that the size of the actual breast is matched with the size of the guide information GI included in the display image DP only at a position where appropriate compression can be performed. For example, in a case in which the guide information GI is smaller than the compression plate 40 as in the display image DP corresponding to a case in which the projection distance is D1 (=300 mm) and the magnification M is 0.75 in FIG. 14, it is easy to see that the compression pressure applied to the breast is insufficient. For example, in a case in which the guide information GI is larger than the compression plate 40 as in the display image DP corresponding to a case in which the projection distance is D3 (=600 mm) and the magnification M is 1.5 in FIG. 14, it is easy to see that the compression pressure is too high.

Therefore, as illustrated in FIGS. 14 and 15, the generation unit 64 may not enlarge or reduce the guide information GI according to the projection distance D indicated by the distance information and may enlarge or reduce the imaging information RI according to the projection distance D indicated by the distance information. That is, the projection control unit 66 may perform control to project the imaging information RI having a size corresponding to the projection distance D indicated by the distance information onto the projection surface.

Figure 16:
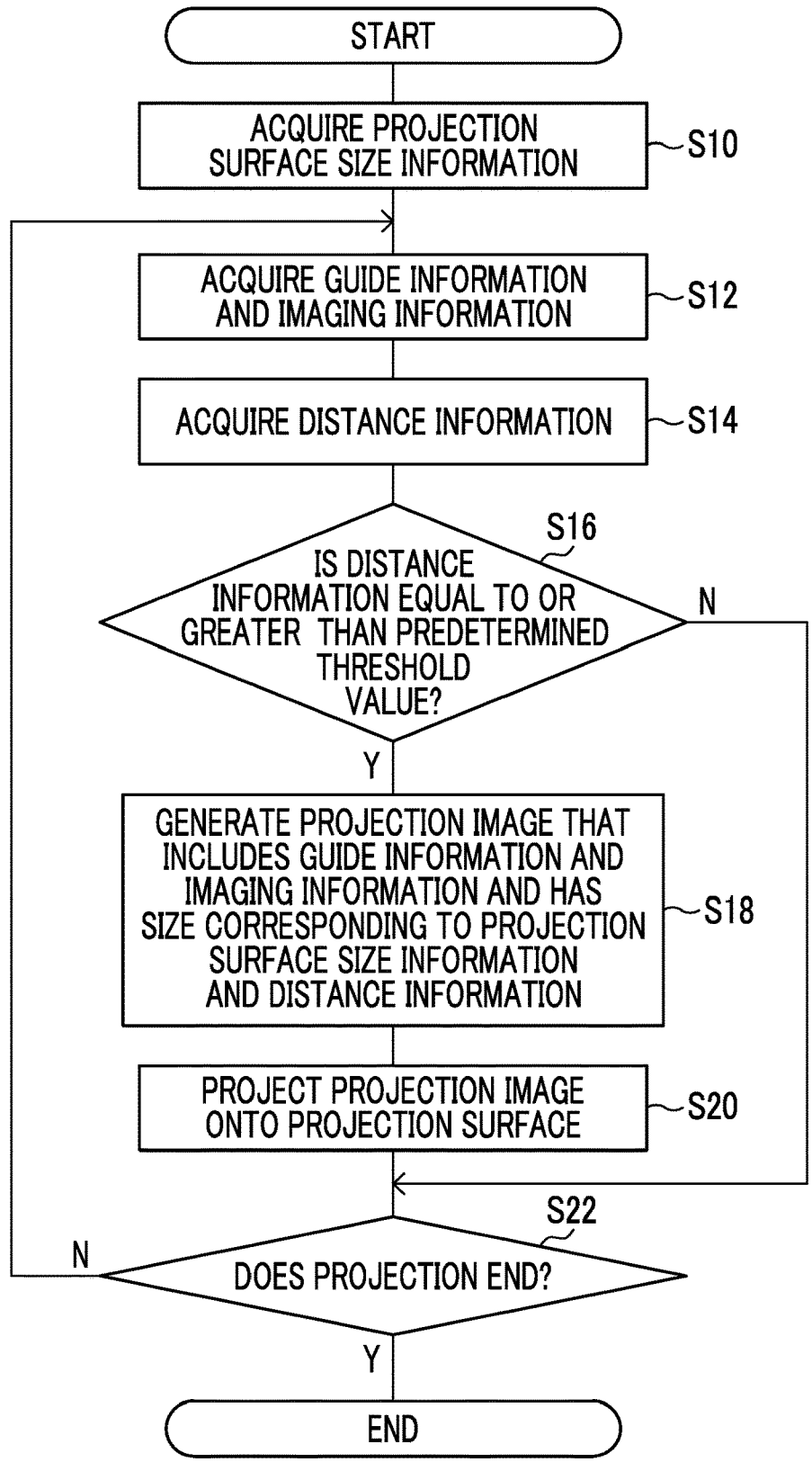
FIG. 16 is a flowchart illustrating an example of the flow of information processing according to a first embodiment.

Next, the operation of the console 12 according to this embodiment will be described with reference to FIG. 16. For example, in a case in which the console 12 receives an imaging order from the RIS 2 or the like, the CPU 50A of the control unit 50 executes the information processing program 51 stored in the ROM 50B to perform the information processing whose example is illustrated in FIG. 16. FIG. 16 is a flowchart illustrating an example of the flow of the information processing performed in the console 12 according to this embodiment.

In Step S10 of FIG. 16, the acquisition unit 60 acquires the projection surface size information indicating the size of the projection surface. In Step S12, the acquisition unit 60 acquires the guide information GI and the imaging information RI. In Step S14, the acquisition unit 60 acquires the distance information indicating the projection distance D.

In Step S16, the generation unit 64 determines whether or not the projection distance D indicated by the distance information acquired in Step S14 is equal to or greater than a predetermined threshold value. In a case in which the determination result in Step S16 is "Yes", in Step S18, the generation unit 64 generates the projection image PP having a size corresponding to the projection surface size information acquired in Step S10 and the projection distance D indicated by the distance information acquired in Step S14. In addition, the projection image PP includes the guide information GI and the imaging information RI acquired in Step S12.

In Step S20, the projection control unit 66 performs control to project the projection image PP generated in Step S18 onto the projection surface of the compression plate 40. In a case in which Step S20 is ended and the determination result in Step S16 is "No", the process proceeds to Step S22. In Step S22, the projection control unit 66 determines whether or not to ends the projection. In a case in which the projection is continued (N in Step S22), the process returns to Step S12. On the other hand, in a case in which the projection is ended (Y Step S22), the process ends. In addition, it is determined that the projection is ended at a predetermined timing such as the operation of the operation unit 56 by the user and the completion of the imaging.

As described above, the console 12 according to this embodiment comprises the CPU 50A which corresponds to at least one processor. The CPU 50A acquires the distance information indicating the projection distance D, which is the distance from the projector 39 that projects the projection image PP onto the projection surface of the compression plate 40 to the projection surface, in the mammography apparatus 10 that irradiates the breast compressed by the compression plate 40 with the radiation R to capture a radiographic image. Further, in a case in which the projector 39 projects the projection image PP at the magnification M corresponding to the projection distance D, the CPU 50A performs control to direct the projector 39 to project the projection image PP having a size corresponding to the projection distance D indicated by the distance information onto the projection surface. Therefore, according to the console 12 of this embodiment, even in a case in which the compression plate 40 is moved in the up-down direction, it is possible to display the display image DP having an appropriate size.

In the above-described embodiment, instead of the projection distance D, information indicating the height of the compression plate 40 may be used as the distance information. The height of the compression plate 40 may be represented by, for example, the distance between the imaging surface 30A (imaging table 30) and the contact surface 43B (the bottom portion 43 of the compression plate 40), the distance between the radiation source 37R and the contact surface 43B (the bottom portion 43 of the compression plate 40), and the amount of driving of the compression plate driving unit from the reference position.

Further, in the above-described embodiment, information indicating the height of the compression plate 40 may be used instead of the information indicating the thickness of the breast in the compression direction in which the breast is compressed. The height of the compression plate 40 may be represented by, for example, the distance between the imaging surface 30A (imaging table 30) and the contact surface 43B (the bottom portion 43 of the compression plate 40), the distance between the radiation source 37R and the contact surface 43B (the bottom portion 43 of the compression plate 40), and the amount of driving of the compression plate driving unit from the reference position.

Second Embodiment

In some cases, the compression portion 42 of the compression plate 40 can be moved (shifted) in the plane direction of the contact surface 43B with the breast in the mammography apparatus 10. In other words, the plane direction is a direction in the XY plane of FIG. 2, that is, a direction from the chest wall to the nipple of the subject and the left-right direction of the breast. The configuration in which the compression plate 40 can be moved in the plane direction is not particularly limited. For example, a configuration may be used in which a moving mechanism, such as a rail, is provided in the support portion 46 of the compression plate 40 and the compression portion 42 can be moved relative to the support portion 46. Further, for example, the compression plate driving unit may move the compression plate 40 in the plane direction, in addition to the up-down direction.

Figure 17:
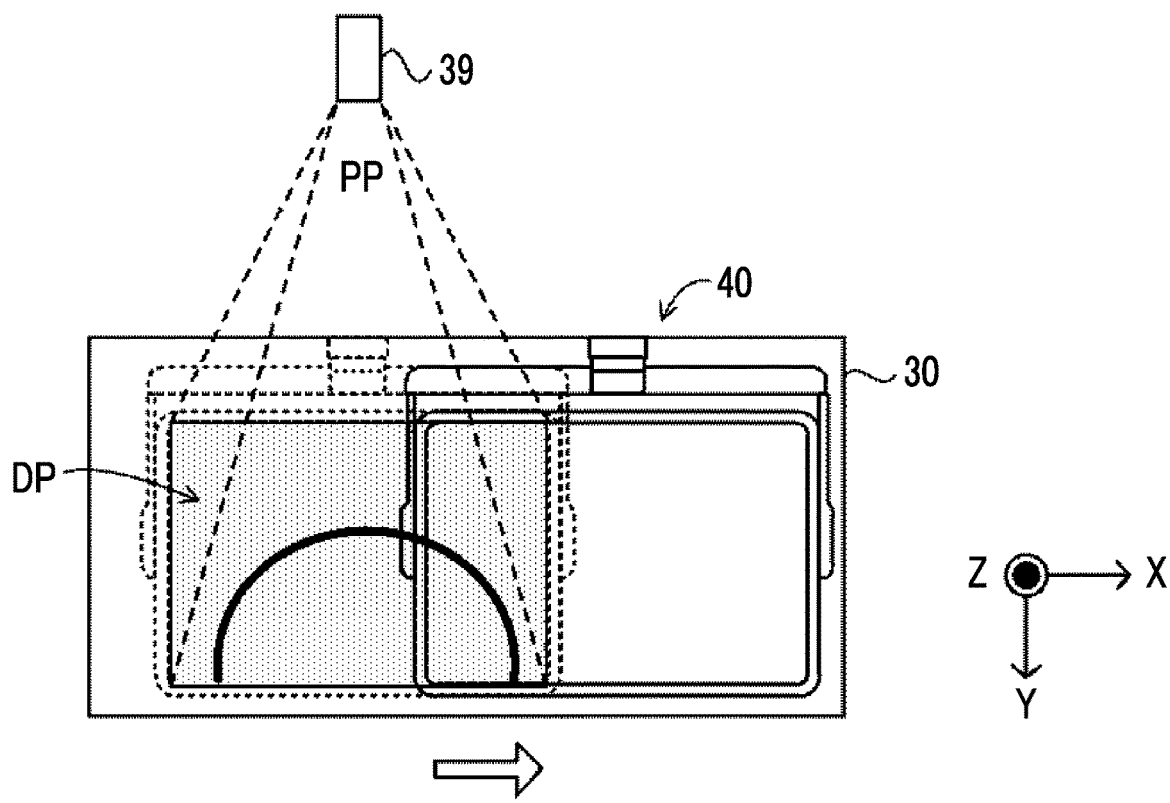
FIG. 17 is a diagram illustrating a method for projecting a projection image onto a compression plate that is moved in a plane direction.
Figure 18:
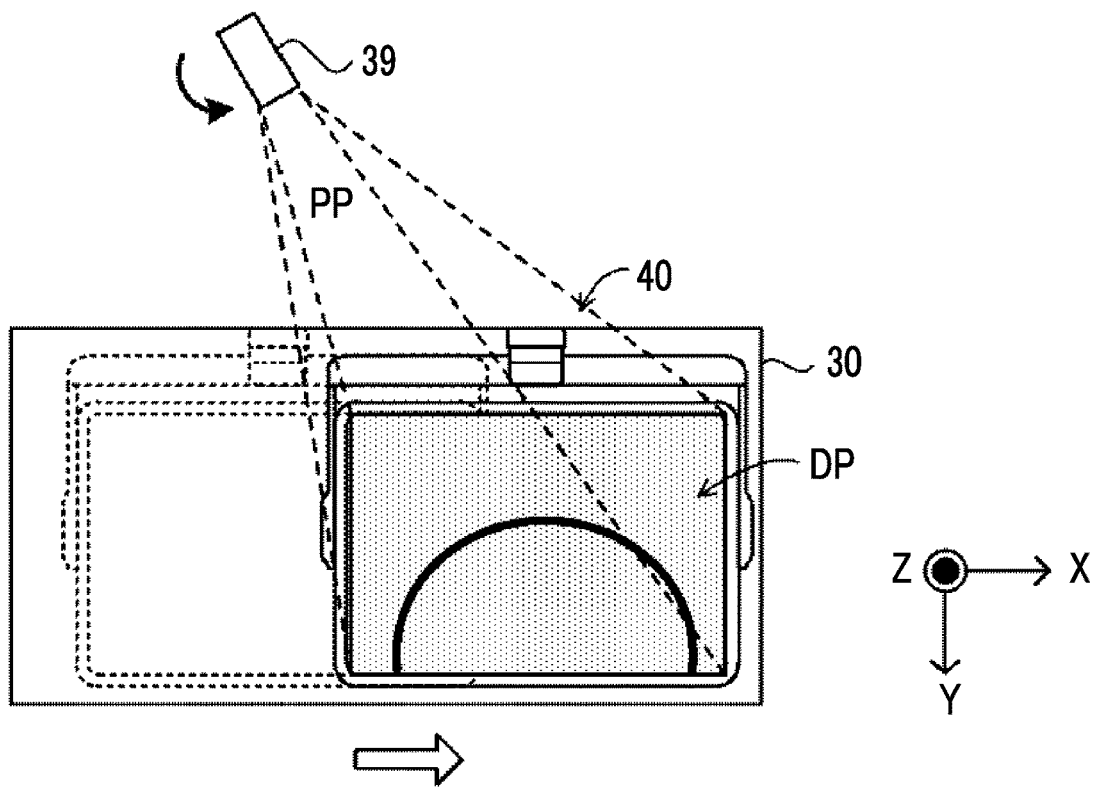
FIG. 18 is a diagram illustrating the method for projecting the projection image onto the compression plate that is moved in the plane direction.
Figure 19:
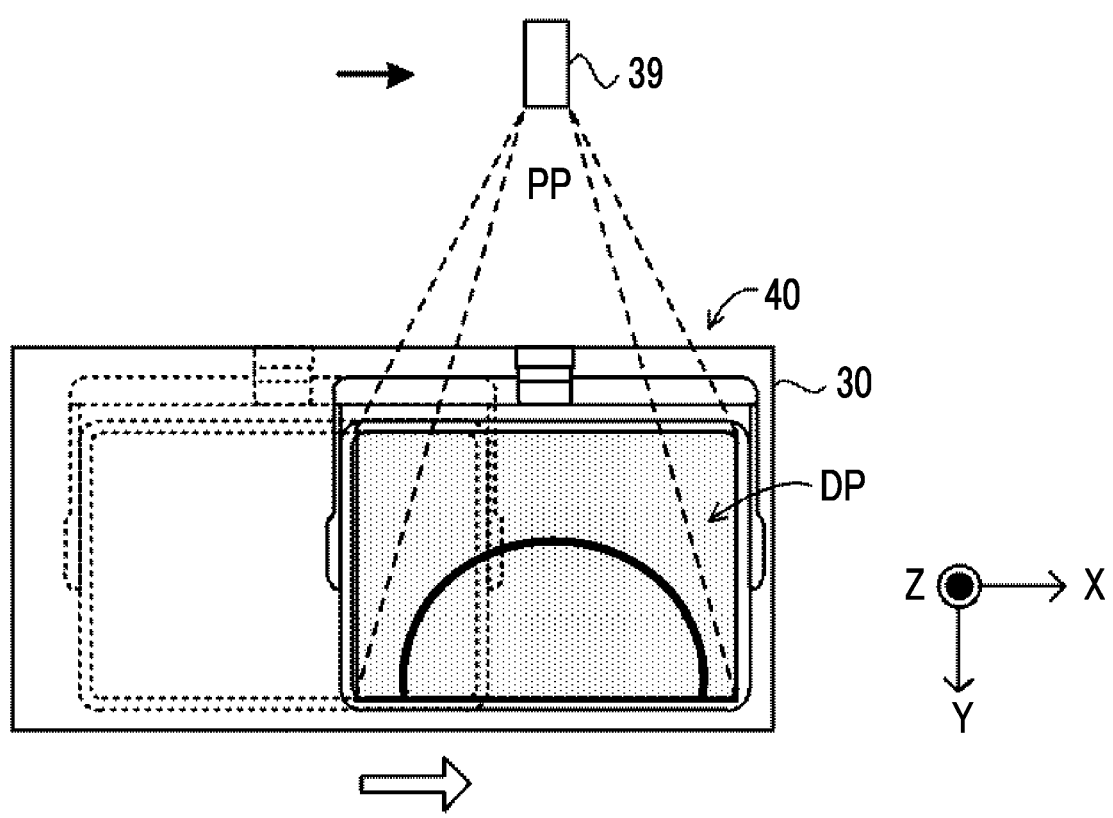
FIG. 19 is a diagram illustrating the method for projecting the projection image onto the compression plate that is moved in the plane direction.

Next, the functions of the console 12 according to this embodiment will be described with reference to FIGS. 17 to 19. FIGS. 17 to 19 are diagrams schematically illustrating a state in which the compression plate 40 is moved in the direction of a white arrow from a position before movement represented by a dotted line to a position after movement represented by a solid line.

As illustrated in FIG. 17, in a case in which the compression plate 40 is moved in the plane direction and the position of the projection image PP projected by the projector 39 is not changed, the display image DP may not be displayed on the projection surface of the moved compression plate 40. Therefore, the console 12 according to this embodiment has a function that can project the projection image PP onto the projection surface of the compression plate 40, following the movement of the compression plate 40, even in a case in which the compression plate 40 is moved in the plane direction. Hereinafter, the same configurations as those in the first embodiment are denoted by the same reference numerals, and the description thereof will not be repeated.

The projector 39 according to this embodiment is configured such that at least one of a projection direction in the plane direction or a projection position in the plane direction can be changed. In a case in which the projection direction of the projector 39 in the plane direction can be changed, as illustrated in FIG. 18, the projection image PP can be projected following the movement of the compression plate 40 in the plane direction. In addition, in a case in which the projection position of the projector 39 in the plane direction can be changed, as illustrated in FIG. 19, the projection image PP can be projected following the movement of the compression plate 40 in the plane direction. In addition, for example, these configurations may be combined such that the projection position of the projector 39 is changed to respond to the rough movement of the compression plate 40 (for example, in units of 10 mm) and the projection direction of the projector 39 is changed to respond to the fine movement of the compression plate 40 (for example, in units of 1 mm).

The specific configuration of the projector 39 is not particularly limited. For example, the mammography apparatus 10 may comprise a driving unit that can change the projection direction of the projector 39 and the position of the projector 39 in the XY plane. Further, for example, the mammography apparatus 10 may comprise a mirror that bends the optical path of the projection image PP projected from the projector 39 and may adjust the angle of the mirror to change the projection direction in the plane direction. Furthermore, for example, the projector 39 may comprise a known lens shift function of moving the position of a projection lens in the plane direction, and the projection direction in the plane direction may be changed by the lens shift function.

The acquisition unit 60 acquires positional information indicating the position of the compression plate 40 in the plane direction. A unit for acquiring the positional information is not particularly limited. For example, the acquisition unit 60 may detect the amount of movement of the compression plate 40 from the reference position in the plane direction using a sensor, which detects the amount of movement of the compression plate 40 in the plane direction and is provided in the compression unit 36, and may derive the positional information. Further, for example, the acquisition unit 60 may detect the position coordinates of the compression plate 40 in the plane direction using a device, such as a TOF camera, that measures the distance to an object to be imaged and may derive the positional information. In the distance image captured by the TOF camera, each pixel has distance information indicating the distance between the TOF camera and the object to be imaged. Since the distance information is different between the pixel corresponding to the compression plate 40 and the pixel corresponding to the imaging table 30 (that is, a portion in which the compression plate 40 is not present), the capture of the image of the imaging table 30 including the compression plate 40 by the TOF camera also makes it possible to acquire the positional information of the compression plate 40.

In addition, the projection control unit 66 performs control to direct the projector 39 to project the projection image PP onto the projection surface of the compression plate 40 whose position has been specified on the basis of the positional information. Specifically, the projection control unit 66 controls the projection direction of the projector 39 and the position of the projector 39 according to the positional information.

Further, in a case in which the projection direction of the projector 39 is changed, the display image DP may be distorted and displayed on the projection surface. In this case, the generation unit 64 may deform and generate the projection image PP in advance so as to correct the distortion corresponding to the projection direction.

Figure 20:
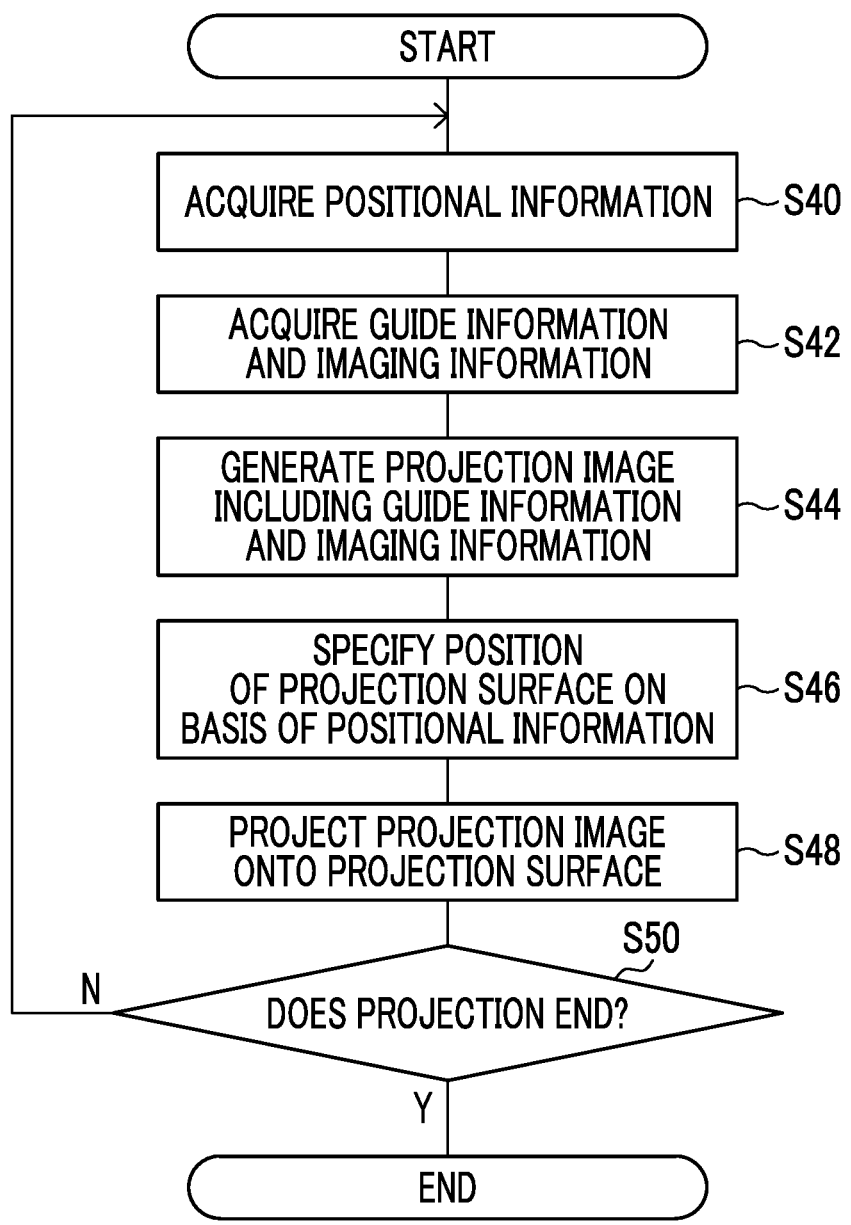
FIG. 20 is a flowchart illustrating an example of the flow of information processing according to a second embodiment.

Next, the operation of the console 12 according to this embodiment will be described with reference to FIG. 20. For example, in a case in which the console 12 receives an imaging order from the RIS 2 or the like, the CPU 50A of the control unit 50 executes the information processing program 51 stored in the ROM 50B to perform the information processing whose example is illustrated in FIG. 20. FIG. 20 is a flowchart illustrating an example of the flow of the information processing performed in the console 12 according to this embodiment.

In Step S40 of FIG. 20, the acquisition unit 60 acquires positional information indicating the position of the compression plate 40 in the plane direction. In Step S42, the acquisition unit 60 acquires the guide information GI and the imaging information RI. In Step S44, the generation unit 64 generates the projection image PP including the guide information GI and the imaging information RI acquired in Step S42.

In Step S46, the projection control unit 66 specifies the position of the projection surface of the compression plate 40 in the plane direction on the basis of the positional information acquired in Step S40. In Step S48, the projection control unit 66 performs control to project the projection image PP generated in Step S44 onto the projection surface whose position has been specified in Step S46. In Step S50, the projection control unit 66 determines whether or not to end the projection. In a case in which the projection is continued (N in Step S50), the process returns to Step S40. On the other hand, in a case in which the projection is ended (Yin Step S50), the process ends. In addition, it is determined that the projection is ended at a predetermined timing such as the operation of the operation unit 56 by the user and the completion of the imaging.

As described above, the console 12 according to this embodiment comprises the CPU 50A which corresponds to at least one processor. The CPU 50A acquires the positional information indicating the position of the compression plate 40 in the plane direction in the mammography apparatus 10 that irradiates the breast compressed by the compression plate 40, which is configured to be movable in the plane direction of the contact surface 43B with the breast, with the radiation R to capture a radiographic image. Further, the projection control unit 66 performs control to direct the projector 39, which projects the projection image PP onto the projection surface of the compression plate 40, to project the projection image PP onto the projection surface of the compression plate 40 whose position has been specified on the basis of the positional information. Therefore, according to the console 12 of this embodiment, even in a case in which the compression plate 40 is moved in the plane direction of the contact surface 43B with the breast, it is possible to display the display image DP on the compression plate.

In addition, the technology according to this embodiment and the technology according to the first embodiment may be appropriately combined with each other. For example, the console 12 may generate the projection image PP having a size corresponding to the projection distance D indicated by the distance information according to the movement of the compression plate 40 in the up-down direction and may control the projector 39 such that the projection image PP is projected at a position corresponding to the positional information according to the movement of the compression plate 40 in the plane direction.

Third Embodiment

Figure 21:
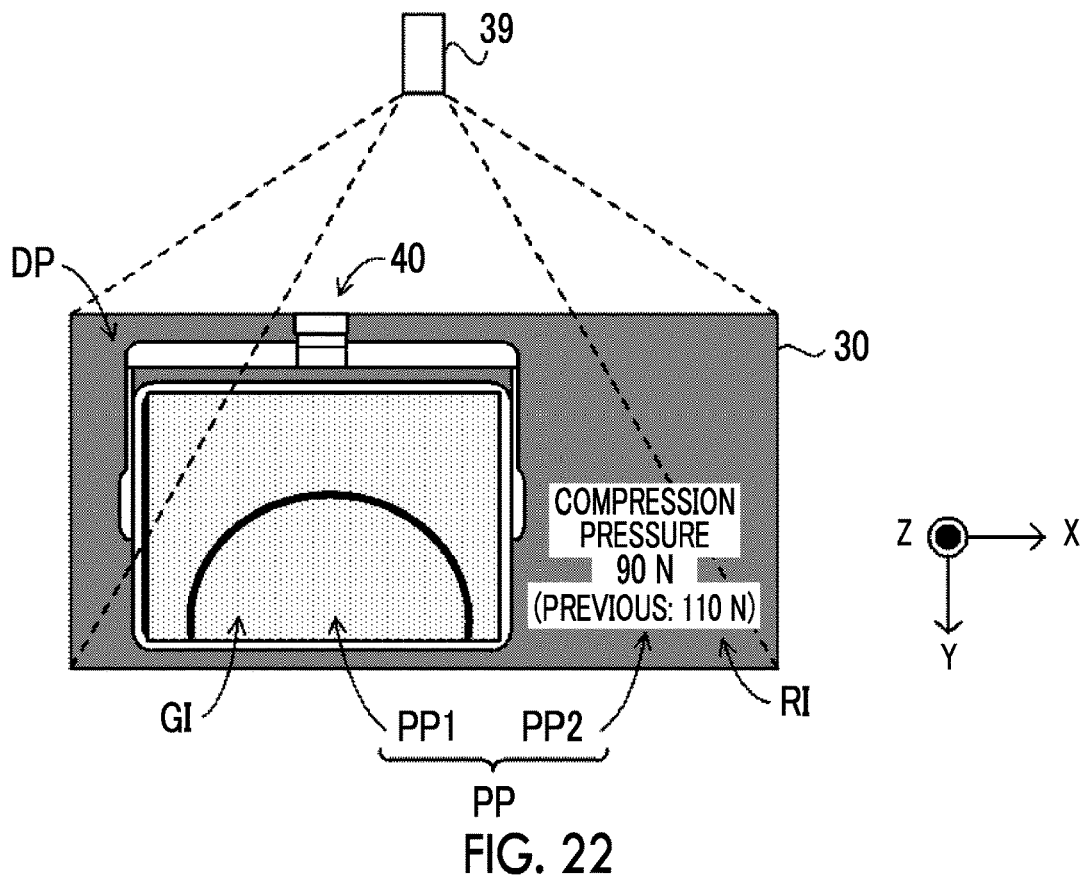
FIG. 21 is a diagram illustrating a projection image that has different contents in regions inside and outside a projection surface of the compression plate.
Figure 22:
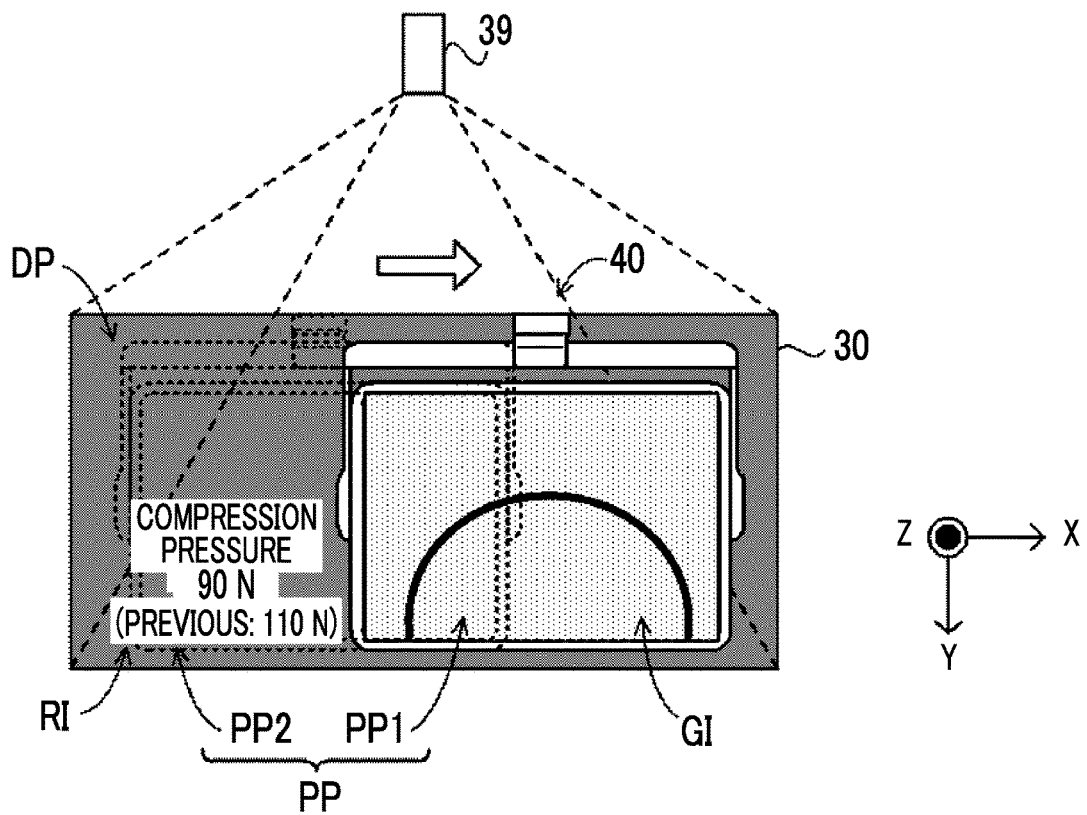
FIG. 22 is a diagram illustrating a method for projecting the projection image onto the compression plate that is moved in the plane direction.

Another configuration will be described in which the projection image PP is projected onto the projection surface following the movement of the compression plate 40 in a case in which the compression plate 40 is configured to be movable in the plane direction of the contact surface 43B with the breast as in the second embodiment. Next, the functions of a console 12 according to this embodiment will be described with reference to FIGS. 21 and 22. FIGS. 21 and 22 are diagrams illustrating a state in which the projection image PP is projected onto the projection surface of the compression plate 40 and the imaging table 30. As illustrated in FIG. 21, the console 12 according to this embodiment has a function of projecting the projection image PP in which a first portion PP1 projected inside the projection surface of the compression plate 40 and a second portion PP2 projected onto a region outside the projection surface have different contents. Hereinafter, the same configurations as those in the first and second embodiments are denoted by the same reference numerals, and the description thereof will not be repeated.

The projector 39 according to this embodiment is configured to project the projection image PP onto a projection region including at least the projection surface of the compression plate 40. That is, the projector 39 can project the projection image PP onto a region outside the projection surface of the compression plate 40 such as the imaging table 30 or the like.

The acquisition unit 60 acquires positional information indicating the position of the compression plate 40 in the plane direction. The generation unit 64 divides the projection image PP into two portions PP1 and PP2 on the basis of the positional information acquired by the acquisition unit 60. Specifically, the generation unit 64 generates the projection image PP in which the first portion PP1 projected onto a region inside the projection surface and the second portion PP2 projected onto a region outside the projection surface have different contents. For example, FIG. 21 illustrates the projection image PP in which the first portion PP1 includes the guide information GI and the second portion PP2 includes information indicating compression pressure as an example of the imaging information RI.

Further, in a case in which the positional information acquired by the acquisition unit 60 changes, the generation unit 64 may regenerate the projection image PP in which the ranges of the first portion PP1 and the second portion PP2 have been changed following a change in the position of the compression plate 40 specified on the basis of the positional information. For example, FIG. 22 illustrates a state in which the compression plate 40 is moved to the right from the state illustrated in FIG. 21. As illustrated in FIG. 22, the generation unit 64 regenerates the projection image PP such that the first portion PP1 is projected at the position of the projection surface of the compression plate 40 after the movement.

In addition, the generation unit 64 may generate the projection image PP in which at least one of hue, saturation, brightness, or luminance is different between the first portion PP1 and the second portion PP2. For example, the first portion PP1 may include at least one of the guide information GI or the imaging information RI, and the second portion PP2 may include at least one of the guide information GI or the imaging information RI which differs from that in the first portion PP1 in at least one of hue, saturation, brightness, or luminance. Further, for example, the first portion may include at least one of the guide information GI or the imaging information RI represented by characters, and the second portion may include a one-color solid image. According to these aspects, since the first portion PP1 and the second portion PP2 can be easily distinguished, it is possible to improve visibility.

Further, the projection control unit 66 performs control to direct the projector 39 to project the projection image PP onto the projection region.

Figure 23:
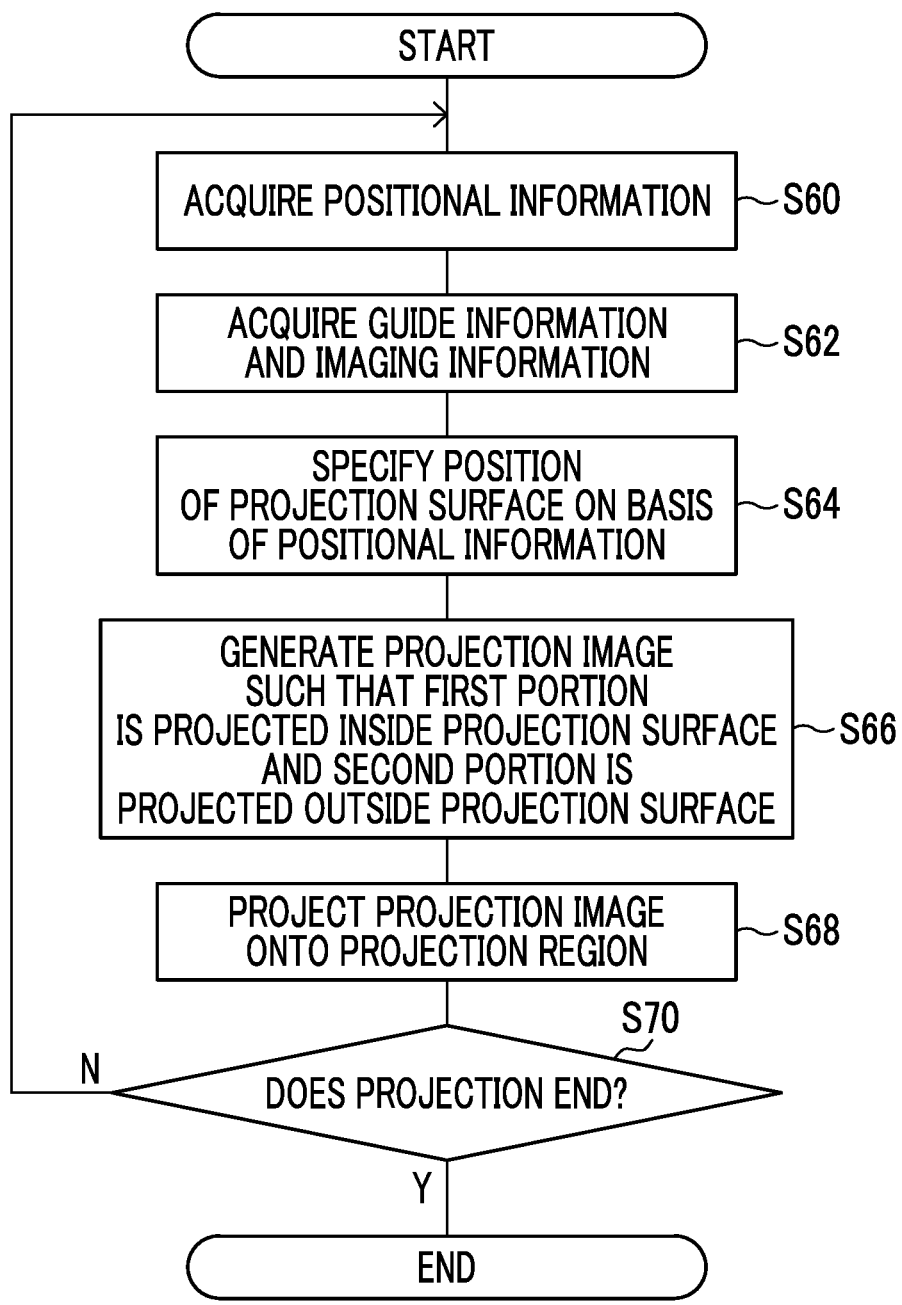
FIG. 23 is a flowchart illustrating an example of the flow of information processing according to a third embodiment.

Next, the operation of the console 12 according to this embodiment will be described with reference to FIG. 23. For example, in a case in which the console 12 receives an imaging order from the RIS 2 or the like, the CPU 50A of the control unit 50 executes the information processing program 51 stored in the ROM 50B to perform the information processing whose example is illustrated in FIG. 23. FIG. 23 is a flowchart illustrating an example of the flow of the information processing performed in the console 12 according to this embodiment.

In Step S60 of FIG. 23, the acquisition unit 60 acquires positional information indicating the position of the compression plate 40 in the plane direction. In Step S62, the acquisition unit 60 acquires the guide information GI and the imaging information RI. In Step S64, the generation unit 64 specifies the position of the projection surface of the compression plate 40 in the plane direction on the basis of the positional information acquired in Step S60. In Step S66, the generation unit 64 generates the projection image PP such that the first portion PP1 is projected in the projection surface of the compression plate 40 specified in Step S64 and the second portion PP2 is projected outside the projection surface.

In Step S68, the projection control unit 66 performs control to project the projection image PP generated in Step S66 onto the projection region. In Step S70, the projection control unit 66 determines whether or not to end the projection. In a case in which the projection is continued (N in Step S70), the process returns to Step S60. On the other hand, in a case in which the projection is ended (Y in Step S70), the process ends. In addition, it is determined that the projection is ended at a predetermined timing such as the operation of the operation unit 56 by the user and the completion of the imaging.

As described above, the console 12 according to this embodiment comprises the CPU 50A which corresponds to at least one processor. The CPU 50A performs control to direct the projector 39, which projects the projection image PP onto the projection region including at least the projection surface of the compression plate 40, to project the projection image PP, in which the first portion PP1 projected onto a region inside the projection surface and the second portion PP2 projected onto a region outside the projection surface have different contents, onto the projection region in the mammography apparatus 10 that irradiates the breast compressed by the compression plate 40 with the radiation R to capture a radiographic image. Therefore, according to the console 12 of this embodiment, even in a case in which the compression plate 40 is moved in the plane direction of the contact surface 43B with the breast, it is possible to display the display image DP on the compression plate.

In addition, the technology according to this embodiment and the technology according to the first embodiment may be appropriately combined with each other. For example, the console 12 may generate the projection image PP having a size corresponding to the projection distance D indicated by the distance information according to the movement of the compression plate 40 in the up-down direction and may control the projector 39 such that the projection image PP in which the ranges of the first portion and the second portion have been changed according to the movement of the compression plate 40 in the plane direction is projected.

Further, in the above-described embodiment, the aspect in which the technology according to this embodiment is applied in a case in which the compression plate 40 can be moved in the plane direction of the contact surface 43B has been described. However, the present disclosure is not limited thereto. For example, the technology according to this embodiment may be applied to the compression plate 40 whose position in the plane direction is fixed (is not moved). In this case, it is considered that the position of the compression plate 40 in the plane direction is fixed to a predetermined position. Therefore, the acquisition unit 60 may not acquire the positional information. The generation unit 64 may generate the projection image PP such that the first portion PP1 is projected onto a predetermined region inside the projection surface of the compression plate 40 and the second portion PP2 is projected onto a predetermined region outside the projection surface.

Configuration of Compression Plate 40 Capable of Projecting Light

The configuration of the compression plate 40 onto which the projection image PP can be projected by the projector 39 will be described as a configuration common to the first and second embodiments with reference to FIGS. 24 to 28. As described above, in this embodiment, the compression portion 42 of the compression plate 40 is configured to include a material that is optically transparent in order to perform positioning and to check the compressed state in the compression of the breast. In a case in which light is incident on a transparent object, most (for example, 90%) of the light is transmitted, and a portion (for example, 10%) of the light is specularly reflected from the surface of the object such that an incident angle and a reflection angle are equal to each other. In practice, light absorption occurs in the object, and scattering occurs at the interface of the object and in the object. However, they will be ignored here. Light reflected from the surface of the object enters the eyes, and the observer can see light projected onto the surface of the object. That is, even in the compression plate 40 configured to include a transparent material, in a case in which the projection image PP projected by the projector 39 is reflected from the projection surface of the compression plate 40 and the reflected light enters the eyes of the observer, the observer can visually recognize the image displayed on the projection surface.

Figure 24:
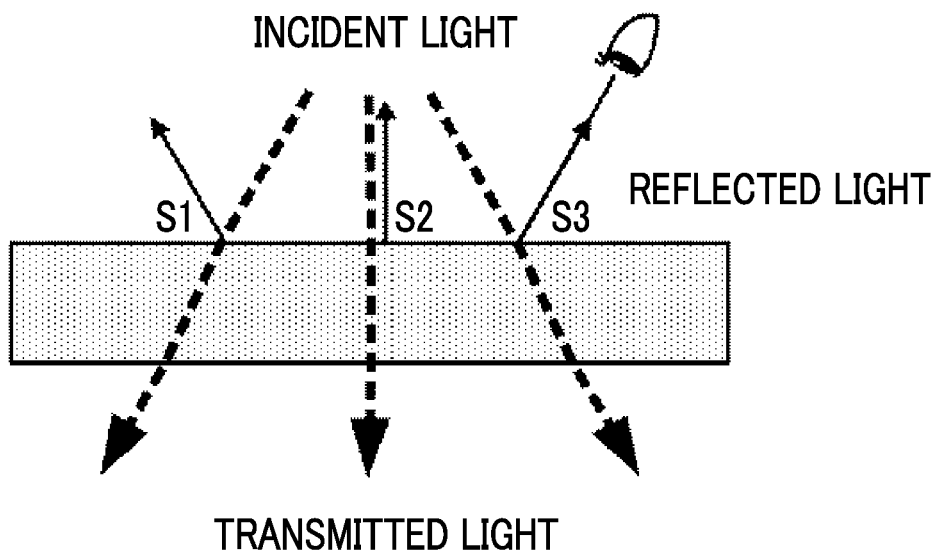
FIG. 24 is a diagram illustrating the principle of reflection from a smooth flat surface.
Figure 25:
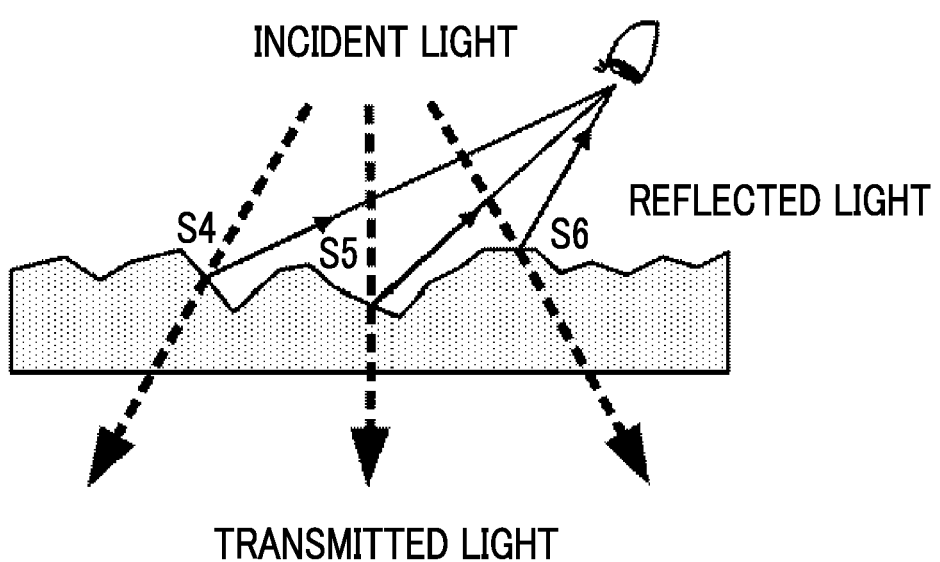
FIG. 25 is a diagram illustrating the principle of reflection from a roughened surface.
Figure 26:
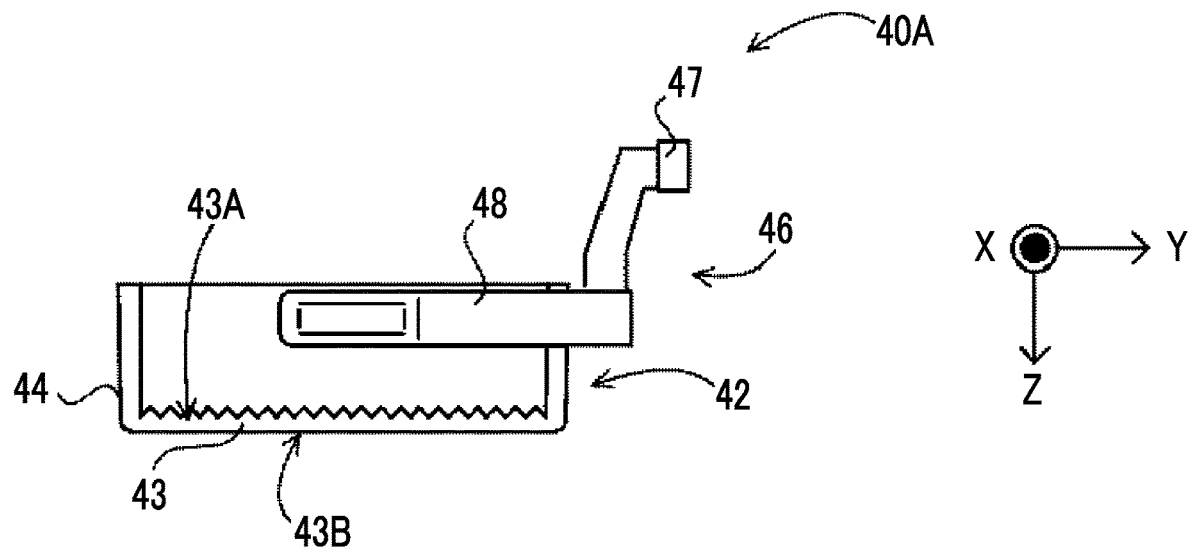
FIG. 26 is a diagram schematically illustrating an example of a compression plate having a roughened projection surface.

FIG. 24 is a diagram illustrating an example of the direction of the reflected light in a case in which incident light is incident on a smooth flat surface. FIG. 25 is a diagram illustrating an example of the direction of the reflected light in a case in which incident light is incident on an uneven surface. In FIGS. 24 and 25, three incident light components are illustrated as representatives. As illustrated in FIGS. 24 and 25, light incident on each of positions S1 to S6 on the surface of the object is specularly reflected, regardless of whether the surface of the object is a smooth flat surface or an uneven surface.

As illustrated in FIG. 24, in a case in which the surface of the object is a smooth flat surface, among the reflected light components at the positions S1 to S3, only the reflected light at the position S3 where the angle (incident angle) with respect to the light source and the angle (reflection angle) with respect to the eyes are equal to each other enters the eyes of the observer. In the eyes of the observer, light is displayed only at the position S3 on the surface of the object and is not displayed at the other positions S1 and S2. That is, in a case in which the projection surface of the compression plate 40 is a smooth flat surface, a display image is not displayed on the projection surface even though the projection image PP is projected onto the projection surface by the projector 39.

On the other hand, as illustrated in FIG. 25, in a case in which the surface of the object is an uneven surface and the angles of the reflecting surfaces at the positions S4 to S6 are different, the angle (incident angle) with respect to the light source and the angle (reflection angle) with respect to the eyes can be equal to each other at each of the positions S4 to S6. In this case, since the reflected light from the positions S4 to S6 enters the eyes of the observer, light is displayed at each of the positions S4 to S6 on the surface of the object in the eyes of the observer. That is, in a case in which the projection surface of the compression plate 40 is an uneven surface and the projection image PP is projected onto the projection surface by the projector 39, the display image is displayed on the projection surface.

Therefore, it is preferable to perform a roughening process on the projection surface of the compression plate 40 in this embodiment such that the observer can visually recognize the display image in a case in which the projection image PP is projected by the projector 39. The roughening process is a process that forms unevenness on the surface of the projection surface. Examples of the roughening process include a surface texturing process and a satin finishing process. A roughening method is not particularly limited, and various known methods, such as a mechanical roughening process, an electrochemical roughening process, and a chemical roughening process, may be used.

Specifically, at least a partial region of at least one surface of the compression plate 40 which does not come into contact with the breast and onto which the projection image PP can be projected by the projector 39 is roughened. For example, in a case in which the skin line image is projected so as to be superimposed on the breast, at least a partial region of the surface (the upper surface 43A of the bottom portion 43 in FIG. 26) which is opposite to the contact surface 43B with the breast is roughened as illustrated in a schematic diagram of FIG. 26. In addition, even in a case in which the contact surface 43B of the bottom portion 43 with the breast is roughened, the display image is displayed on the bottom portion 43. However, it is desirable that the contact surface 43B with the breast is not roughened in order to suppress discomfort caused by the contact of the unevenness with the skin of the subject.

Figure 27:
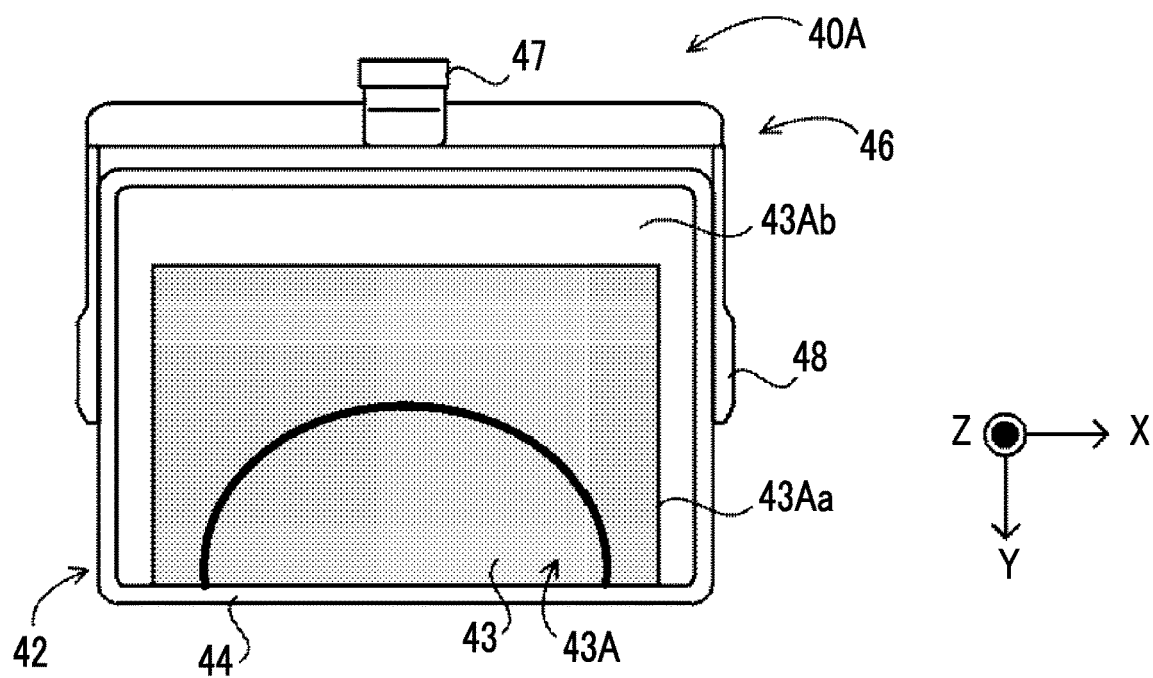
FIG. 27 is a diagram schematically illustrating an example of a compression plate in which a partial region of a projection surface is roughened.
Figure 28:
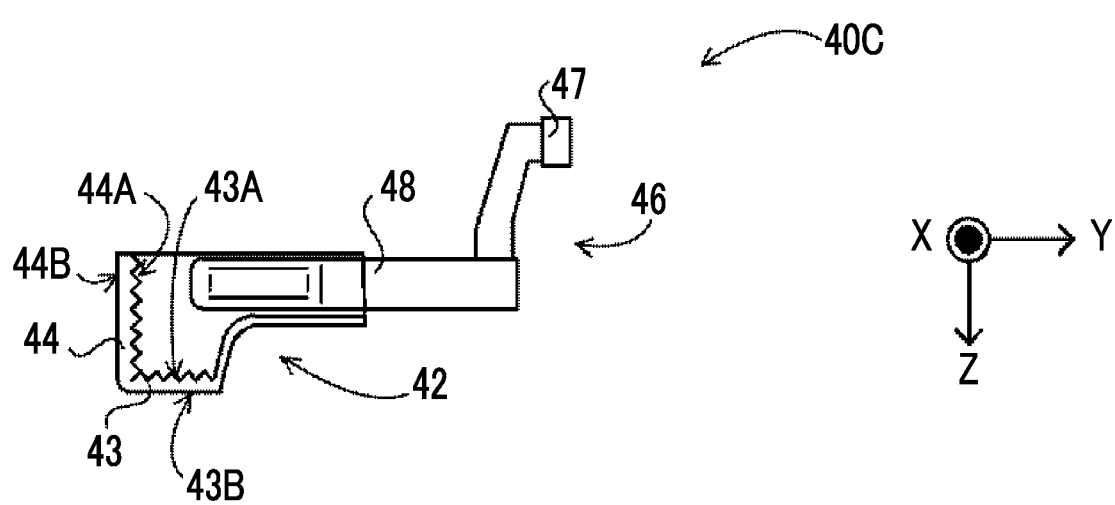
FIG. 28 is a diagram schematically illustrating an example of a compression plate having a roughened projection surface.

Further, assuming that the skin line image is projected so as to be superimposed on the breast, a skin line image projection region is limited to a region on the chest wall side in the upper surface 43A of the compression plate 40. Therefore, for example, as illustrated in FIG. 27, on the surface (upper surface 43A in FIG. 27) opposite to the contact surface 43B with the breast, a region 43Aa on the chest wall side (the lower side in the Y direction in FIG. 27) may be roughened, and a region 43Ab on the side (the upper side in the Y direction in FIG. 27) opposite to the chest wall may not be roughened. For the same reason, particularly, in the compression plate 40 used for CC imaging, a partial region including the center of the breast in the left-right direction (the X direction in FIG. 27) may be roughened, and the end parts of the breast in the left-right direction (the X direction in FIG. 27) may not be roughened.

Further, for example, in a case in which the projection image PP can be projected onto plural surfaces, at least a partial region of each of the plurality of surfaces that do not come into contact with the breast may be roughened. For example, in a case in which the skin line image is projected onto the bottom portion 43 of the compression plate 40 and character information is projected onto the wall portion 44, a surface (inner surface 44A) that intersects the surface (upper surface 43A) opposite to the contact surface 43B with the breast may be roughened in addition to the upper surface 43A as illustrated in a schematic diagram of FIG. 28. In addition, even in a case in which an outer surface 44B of the wall portion 44 is roughened, the display image is displayed on the wall portion 44. However, it is desirable that the outer surface 44B coming into contact with the chest wall is not roughened in order to suppress discomfort caused by the contact of the unevenness with the skin of the subject.

Further, for example, in a case in which both the bottom portion 43 and the wall portion 44 are small and it is difficult to project the projection image PP onto any surface as in the compression plate 40 for spot imaging, the projection image PP may be projected onto the support portion 46 that supports the compression plate 40. In this case, at least a partial region of at least one surface of the support portion 46 may be roughened.

In addition, in a case in which the region onto which the projection image PP can be projected is limited in each surface onto which the projection image PP is projected, only that region may be roughened.

It is preferable that the degree of roughening is equal to or smaller than the pixel size of the radiation detector 28 such that unevenness is not reflected in the radiographic image. In addition, as the roughness becomes smaller, the reflected light is more likely to diffuse. Therefore, it is possible to increase the visibility of the display image on the projection surface. On the other hand, in a case in which the roughness is too small, the breast is not seen through the compression plate. Therefore, it is preferable that the roughening is performed to the extent that the positioning of the breast is not hindered.

Specifically, in a case in which the projection surface of the compression plate 40 and the support portion 46 are configured to include the above-mentioned transparent resin, it is desirable that the arithmetic average roughness (Ra) of each roughened region is equal to or greater than 5 µm and equal to or less than 20 µm. In a case in which the arithmetic average roughness is equal to or less than 20 µm, it is possible to suppress the unevenness from being reflected in the radiographic image and to make it easy to see the display image on the projection surface. In a case in which the arithmetic average roughness is equal to or greater than 5 µm, it is suitable for checking the positioning of the breast through the compression plate 40. In other words, in a case in which the arithmetic average roughness is greater than 20 µm, the unevenness may be reflected in the radiographic image, which makes it difficult to see the display image on the projection surface. In a case in which the arithmetic average roughness is less than 5 µm, it may be difficult to see the breast through the compression plate 40.

As described above, the compression plate 40 according to this embodiment is a compression member that compresses the breast placed between the radiation source and the radiation detector. In the compression plate 40, at least a partial region of at least one surface that does not come into contact with the breast is roughened. Therefore, while the breast can be visually recognized through the compression plate 40, the display image can be displayed in a case in which the projection image PP is projected.

In addition, the use of the compression plate 40 and the support portion 46 whose projection surfaces are roughened such that light can be projected are not limited only to the mammography apparatus 10 according to the first and second embodiments of the present disclosure. The compression plate 40 and the support portion 46 can be used in any mammography apparatus including a radiation source, a radiation detector, a compression member which compresses the breast placed between the radiation source and the radiation detector and in which at least a partial region of at least one surface that does not come into contact with the breast is roughened, and an image projection unit that projects an image onto the roughened region of the compression member.

Further, as the compression plate 40 and the support portion 46 that can project light used in each of the above-described embodiments, the following configurations may be used in addition to the components subjected to the above-mentioned roughening process. For example, a transparent screen (see, for example, JP6606604B) that diffuses and/or reflects light projected by the projector 39 such that a display image can be visibly recognized and transmits light from the front and back surfaces may be attached to the projection surfaces of the compression plate 40 and the support portion 46. In this case, the transparent screen may be attached to the surfaces that come into contact with the skin of the subject, such as the contact surface 43B of the bottom portion 43 and the outer surface 44B of the wall portion 44. That is, the entire surfaces of the compression plate 40 and the support portion 46 can be used as the projection surfaces.

Further, in the first and second embodiments, the aspect in which the projection surface onto which the projection image PP is projected by the projector 39 is at least one surface of the compression plate 40 has been described. However, the present disclosure is not limited thereto. For example, the projector 39 may project the projection image PP onto the imaging table 30 of the mammography apparatus 10 in addition to at least one surface of the compression plate 40.

Further, in each of the above-described embodiments, the example in which the identification information is provided in the compression plate 40, the mammography apparatus 10 reads the identification information, and the acquisition unit 60 acquires the projection surface size information with reference to the identification information and the compression plate information 53 has been described. However, the present disclosure is not limited thereto. For example, the shape of the attached compression plate 40, such as the size of the bottom portion 43 and the height of the wall portion 44, may be measured to directly acquire the projection surface size information of the compression plate 40. For example, a device that measures the distance to an object to be imaged, such as a TOF camera, can be used as a unit for measuring the shape of the compression plate 40. In the distance image captured by the TOF camera, each pixel has distance information indicating the distance between the TOF camera and the object to be imaged. In a case in which the shape of the compression plate 40 as an object to be imaged changes, the distance information of each pixel also changes. Therefore, the type of the compression plate can be identified by capturing the image of the compression plate 40 with the TOF camera.

Further, in each of the above-described embodiments, the aspect in which the console 12 is an example of the information processing device according to the present disclosure has been described. However, devices other than the console 12 may have the functions of the information processing device according to the present disclosure. In other words, for example, the mammography apparatus 10 or an external device other than the console 12 may have some or all of the functions of the acquisition unit 60, the generation unit 64, and the projection control unit 66.

In addition, in each of the above-described embodiments, the aspect in which the radiographic image and the compression plate information 53 are stored in the storage unit 52 of the console 12 has been described. However, the place in which the radiographic image and the compression plate information 53 are stored is not limited to the storage unit 52. For example, the radiographic image and the compression plate information 53 may be stored in the storage unit 22 of the mammography apparatus 10 or may be stored in a device outside the radiography system 1.

Further, in each of the above-described embodiments, for example, the following various processors can be used as the hardware structure of processing units performing various processes such as the acquisition unit 60, the generation unit 64, and the projection control unit 66. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of plural FPGAs or a combination of a CPU and an FPGA). Further, plural processing units may be configured by one processor.

A first example of the configuration in which plural processing units are configured by one processor is an aspect in which one processor is configured by a combination of one or more CPUs and software and functions as plural processing units. A representative example of this aspect is a client computer or a server computer. A second example of the configuration is an aspect in which a processor that implements the functions of the entire system including plural processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the information processing program 51 is stored (installed) in the storage unit 52 in advance has been described. However, the present disclosure is not limited thereto. The information processing program 51 may be recorded on a recording medium, such as a compact disc read only memory (CD-ROM), a digital versatile disc read only memory (DVD-ROM), or a universal serial bus (USB) memory, and then provided. In addition, the information processing program 51 may be downloaded from an external device through a network. Furthermore, the technology of the present disclosure extends to a storage medium that non-temporarily stores the information processing program, in addition to the information processing program.

In the technology of the present disclosure, the above-described embodiments may be appropriately combined with each other. The contents described and illustrated above are detailed descriptions of portions related to the technology of the present disclosure and are merely examples of the technology of the present disclosure. For example, the description of the configurations, functions, operations, and effects is the description of examples of the configurations, functions, operations, and effects of portions related to the technology of the present disclosure. Therefore, unnecessary portions may be deleted or new elements may be added or replaced in the contents described and illustrated above, without departing from the scope and spirit of the technology of the present disclosure.

All of the documents, the patent applications, and the technical standards described in the specification are incorporated by reference herein to the same extent as each individual document, each patent application, and each technical standard are specifically and individually stated to be incorporated by reference.

What is claimed is:

1. An information processing device comprising at least one processor, wherein the processor is configured to:
    acquire distance information indicating a projection distance, which is a distance from an image projection unit that projects a projection image onto a projection surface of a compression member to the projection surface, in a mammography apparatus that irradiates a breast compressed by the compression member with radiation to capture a radiographic image; and
    control the image projection unit such that the projection image having a size corresponding to the projection distance indicated by the distance information is projected onto the projection surface in a case in which the image projection unit projects the projection image at a magnification corresponding to the projection distance;
    wherein the processor is configured to perform control to sequentially project a plurality of the projection images having different sizes onto the projection surface, following a change in the projection distance indicated by the distance information.

2. The information processing device according to claim 1, wherein the processor is configured to perform control to project the projection image having the size corresponding to the projection distance indicated by the distance information onto the projection surface such that a size of a display image displayed on the projection surface by the projection of the projection image at the magnification corresponding to the projection distance by the image projection unit is a predetermined size.

3. The information processing device according to claim 1, wherein, in a case in which an image of the breast as object to be imaged was captured in the past, the processor is configured to acquire, as the distance information, information indicating the projection distance at a time when the image was captured in the past.

4. The information processing device according to claim 1, wherein the processor is configured to perform control such that, each time an amount of change in the projection distance indicated by the distance information is a predetermined amount, the projection image having the size corresponding to the projection distance indicated by the distance information at that time is projected onto the projection surface.

5. The information processing device according to claim 1, wherein the projection image includes guide information that serves as a guide in a case in which the breast is positioned.

6. The information processing device according to claim 1, wherein the projection image includes imaging information represented by characters.

7. The information processing device according to claim 6, wherein the imaging information includes at least one of information indicating a compression pressure of the breast by the compression member, information indicating a thickness of the breast in a compression direction in which the breast is compressed, subject information indicating a subject pertaining to the breast as an object to be imaged, radiographer information indicating a radiographer who performs imaging, date information indicating a date of imaging, or angle information indicating an angle at which an image of the breast is captured.

8. The information processing device according to claim 1, wherein:

the projection image includes guide information that serves as a guide in a case in which the breast is positioned and imaging information represented by characters, and the processor is configured to perform control to project the imaging information having the size corresponding to the projection distance indicated by the distance information onto the projection surface.

9. An information processing device comprising at least one processor, wherein the processor is configured to:

acquire distance information indicating a projection distance, which is a distance from an image projection unit that projects a projection image onto a projection surface of a compression member to the projection surface, in a mammography apparatus that irradiates a breast compressed by the compression member with radiation to capture a radiographic image; and control the image projection unit such that the projection image having a size corresponding to the projection distance indicated by the distance information is projected onto the projection surface in a case in which the image projection unit projects the projection image at a magnification corresponding to the projection distance, wherein the processor is further configured to perform control to stop the projection of the projection image in a case in which the projection distance indicated by the distance information is less than a predetermined threshold value.

10. An information processing device comprising at least one processor, wherein the processor is configured to:

acquire distance information indicating a projection distance, which is a distance from an image projection unit that projects a projection image onto a projection surface of a compression member to the projection surface, in a mammography apparatus that irradiates a breast compressed by the compression member with radiation to capture a radiographic image; and control the image projection unit such that the projection image having a size corresponding to the projection distance indicated by the distance information is projected onto the projection surface in a case in which the image projection unit projects the projection image at a magnification corresponding to the projection distance, wherein the processor is further configured to:

perform control to project the projection image having the size corresponding to the projection distance indicated by the distance information onto the projection surface in a case in which the projection distance indicated by the distance information is constant for a predetermined period; and perform control to stop the projection of the projection image while the projection distance indicated by the distance information is changing.

11. An information processing method comprising:

acquiring distance information indicating a projection distance, which is a distance from an image projection unit that projects a projection image onto a projection surface of a compression member to the projection surface, in a mammography apparatus that irradiates a breast compressed by the compression member with radiation to capture a radiographic image;

controlling the image projection unit such that the projection image having a size corresponding to the projection distance indicated by the distance information is projected onto the projection surface in a case in which the image projection unit projects the projection image at a magnification corresponding to the projection distance;

controlling the image projection unit to sequentially project a plurality of the projection images having different sizes onto the projection surface, following a change in the projection distance indicated by the distance information.

12. A non-transitory computer-readable storage medium storing an image processing program that causes a computer to perform a process comprising:

acquiring distance information indicating a projection distance, which is a distance from an image projection unit that projects a projection image onto a projection surface of a compression member to the projection surface, in a mammography apparatus that irradiates a breast compressed by the compression member with radiation to capture a radiographic image;

controlling the image projection unit such that the projection image having a size corresponding to the projection distance indicated by the distance information is projected onto the projection surface in a case in which the image projection unit projects the projection image at a magnification corresponding to the projection distance;

controlling the image projection unit to sequentially project a plurality of the projection images having different sizes onto the projection surface, following a change in the projection distance indicated by the distance information.

* * * * *